United States Patent
Bianchi et al.

(10) Patent No.: US 10,626,153 B2
(45) Date of Patent: Apr. 21, 2020

(54) HMGB1 VARIANTS AND USES THEREOF

(71) Applicants: Ospedale San Raffaele S.r.l., Milan (MI) (IT); Università degli Studi di Milano—Bicocca, Milan (MI) (IT)

(72) Inventors: Marco Emilio Bianchi, Milan (IT); Maura Casalgrandi, Milan (IT); Emilie Joelle Venereau, Milan (IT); Silvia Brunelli, Milan (IT)

(73) Assignee: OSPEDALE SAN RAFFAELE S.R.L., Milan (MI) (IT)

( * ) Notice: Subject to any disclaimer, the term of this patent is extended or adjusted under 35 U.S.C. 154(b) by 151 days.

(21) Appl. No.: 14/416,128

(22) PCT Filed: Jul. 26, 2013

(86) PCT No.: PCT/EP2013/065829
§ 371 (c)(1),
(2) Date: Jan. 21, 2015

(87) PCT Pub. No.: WO2014/016417
PCT Pub. Date: Jan. 30, 2014

(65) Prior Publication Data
US 2015/0203551 A1 Jul. 23, 2015

Related U.S. Application Data

(60) Provisional application No. 61/676,071, filed on Jul. 26, 2012.

(51) Int. Cl.
*A61K 38/00* (2006.01)
*A61K 38/17* (2006.01)
*C07K 14/47* (2006.01)

(52) U.S. Cl.
CPC ............ *C07K 14/47* (2013.01); *A61K 38/005* (2013.01); *A61K 38/1709* (2013.01)

(58) Field of Classification Search
None
See application file for complete search history.

(56) References Cited

FOREIGN PATENT DOCUMENTS

| WO | 2004/004763 A2 | 1/2004 | | |
|----|----|----|----|----|
| WO | WO 2004004763 A2 * | 1/2004 | ......... | A61K 38/1709 |
| WO | WO-2004004763 A2 * | 1/2004 | ......... | A61K 38/1709 |

OTHER PUBLICATIONS

Yang et al. Redox Modification of Cysteine Residues Regulates the Cytokine Activity of High Mobility Group Box-1 (HMGB1). Molecular Medicine, published online Nov. 7, 2011; 15:250-259.*
Vezzoli et al. Redox remdeling: a candidate regulator of HMGB1 function in injured skeletal muscle. Annals of the New York Academy of Sciences, 2010; 1209:83-90.*
Bowie et al. Deciphering the Message in Protein Sequences: Tolerance to Amino Acid Substitutions. Science, 1990, 247:1306-1310.*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. Journal of Cell Biology, 111:2129-2138, 1990.*
Lazar et al. Transforming Growth Factor ox: Mutation of Aspartic Acid 47 and Leucine 48 Results in Different Biological Activities. Molecular and Cellular Biology; 8(3):1247-1252, 1988.*
Bork. Powers and Pitfalls in Sequence Analysis: The 70% Hurdle. Genome Research, 2000,10:398-400.*
Yang et al. A critical cysteine is required for HMGB1 binding to Toll-like receptor 4 and activation of macrophage cytokine release. PNAS, 2010; 107(26): 11942-11947.*
Kazama et al. Immune Tolerance Induction by Apoptotic Cells Requires Caspase-Dependent Oxidation of HMGB1. Immunity, 2008); 29(1):21-32).*
Kazama et al. Immunity, 2008); 29(1):21-32 (Year: 2008).*
Yang et al. Molecular Medicine, epub Nov. 7, 2011; 15:250-259 (Year: 2011).*
Ottoson et al. Ann Rheum Dis, 2012; 71(Suppl 1):A81). (Year: 2012).*
Vezzoli et al. Annals of the New York Academy of Sciences, 2010; 1209:83-90 (Year: 2010).*
Hoppe, G., et al: "Molecular basis for the redox control of nuclear transport of the structural chromatin protein Hmgb1". Experimental Cell Research, Academic Press, US, vol. 312, No. 18, Aug. 2, 2006 (Aug. 2, 2006),—Nov. 1, 2006 (Nov. 11, 2006), pp. 3526-3538.
Huan Yang, et al: "Molecular Medicine.", vol. 18. No. 2, Nov. 7, 2011 (Nov. 7, 2011),—Jan. 1, 2012 (Jan. 1, 2012), p. 1.
D. Tang, et al: "High-mobility group box 1, oxidative stress, and disease. D,", Antioxid Redox Signal, 14(7), Oct. 24, 2010 (Oct. 24, 2010), pp. 1315-1335. Retrieved from the Internet: URL:http://www.ncbi.nlm.nih.gov/pmc/articles/PMC3048826/pdf/ars.2010.3356.pdf [retrieved on Sep. 18, 2013].
H. Yang, et al: "A critical cysteine is required for HMGBI binding to Toll-like receptor 4 and activation of macrophage cytokine release", Proceedings of the National Academy of Sciences, vol. 107. No. 26, Jun. 29, 2010 (Jun. 29, 2010), pp. 11942-11947.
R. Kang, et al: "The Beclin 1 network regulates autophagy and apoptosis", Cell Death and Differentiation, vol. 18, No. 4, Feb. 11, 2011 (Feb. 11, 2011), pp. 571-580.
Michela Vezzoli, et al: "Redox remodeling: a candidate regulator of HMGB1 function in injured skeletal muscle", Annals of the New York Academy of Sciences, vol. 1209, No. 1, Oct. 19, 2010 (Oct. 19, 2010), pp. 83-90.
E. Venereau, et al: "Mutually exclusive redox forms of HMGBI promote cell recruitment or proinflammatory cytokine release", Molecular Medicine, vol. 18, No. 1, Aug. 27, 2012 (Aug. 27, 2012), pp. 1519-1528.
Semi Park, et al: "Redox State-Dependent Interaction of HMGBI and Cisplatin-Modified DNA", Biochemistry, vol. 50, No. 13, Apr. 5, 2011 (Apr. 5, 2011), pp. 2567-2574.
John Klune, et al: Molecular Medicine., vol. 14, No. 7-8, Apr. 11, 2008 (Apr. 11, 2008), p. 1.

* cited by examiner

*Primary Examiner* — Vanessa L. Ford
*Assistant Examiner* — Sandra E Dillahunt
(74) *Attorney, Agent, or Firm* — Lucas & Mercanti, LLP

(57) ABSTRACT

The present invention relates to HMGB1 variants that maintain HMGB1 wild type chemoattractant function while displaying abolished cytokine and/or chemokine stimulating properties. Such molecules are useful in therapy.

9 Claims, 14 Drawing Sheets

Specification includes a Sequence Listing.

HMGB1 VARIANTS AND USES THEREOF

CROSS-REFERENCE TO RELATED APPLICATIONS

This application is a 371 of PCT/EP2013/065829, filed Jul. 26, 2013, which claims the benefit of U.S. Provisional Application No. 61/676,071, filed Jul. 26, 2012.

TECHNICAL FIELD

The present invention relates to HMGB1 variants that maintain HMGB1 wild type chemoattractant function while displaying abolished cytokine and/or chemokine stimulating properties. Such molecules are useful in therapy.

BACKGROUND ART

Injury can trigger an acute inflammatory response, even in the absence of concomitant infection. "Sterile" inflammation is also associated to several types of cancer. Two events are key for the development of sterile inflammation: the recruitment of leukocytes, especially neutrophils and monocytes, and their activation to release proinflammatory cytokines.

High Mobility Group Box 1 (HMGB1) is a nuclear protein that signals tissue damage when released into the extracellular medium, and thus works as a Damage Associated Molecular Pattern (DAMP) (1). Extracellular HMGB1 can act both as a chemoattractant for leukocytes and as a proinflammatory mediator to induce both recruited leukocytes and resident immune cells to release TNF, IL-1, IL-6 and other cytokines Notably, immune cells secrete HMGB1 when activated by infection or tissue damage (2); mesothelioma and other cancer cells secrete HMGB1 constitutively (Jube et al., 2012).

Recent studies have shown that the proinflammatory cytokine-stimulating activity of HMGB1 depends on the redox state of 3 cysteines: C23 and C45 must form a disulfide bond within the first HMG-box domain of HMGB1, BoxA, whereas the unpaired C106 within BoxB must be in the thiol state (3-5). Both terminal oxidation of these cysteines to sulfonates ($CySO_3^-$) with reactive oxygen species (ROS) and their complete reduction to thiols (CySH) abrogates the cytokine-stimulating activity.

EP 2 068 935 disclose polymer conjugates of HMGB1 and of HMGB1 variants, such polymers are resistant to proteolysis.

There is the need for HMGB1 variants that maintain chemoattractant properties but do not induce cytokine/chemokine production. Such variants may be used to promote the repair and regeneration of the tissue.

SUMMARY OF THE INVENTION

The authors of the present invention surprisingly found that HMGB1 variants in which at least one cysteine is substituted by another amino acid can recruit motile cells. Since the disulfide and thiol states of cysteines are mutually exclusive, the cytokine-stimulating and chemotactic activities of HMGB1 should also be mutually exclusive, which is what the authors show experimentally. HMGB1 terminally oxidized to sulfonates has no activity either as a chemoattractant or in cytokine stimulation. Replacement of all 3 cysteines with serines makes HMGB1 non-oxidizable, thus preventing both its cytokine-stimulating activity and its eventual inactivation, but preserving the chemoattractant activity. Non-oxidizable HMGB1, being unable to trigger inflammation, has favourable properties in recruiting tissue-regenerating macrophages, and in promoting the recruitment of muscle-resident stem cells. Unexpectedly, however, non-oxidizable HMGB1 also limits cell death in the tissue following damage. All of these properties make non-oxidizable HMGB1 a promising tool for limiting tissue damage after injuries and promoting healing.

Tissue damage causes inflammation, by recruiting leukocytes and activating them to release pro-inflammatory mediators. The authors show that High Mobility Group Box 1 protein (human HMGB1, SEQ ID No. 1)

```
mgkgdpkkpr gkmssyaffv qtcreehkkk hpdasvnfse fskkcserwk tmsakekgkf edmakadkar yeremktyip pkgetkkkfk dpnapkrpps afflfcseyr pkikgehpgl sigdvakklg emwnntaadd kqpyekkaak lkekyekdia ayrakgkpda akkgvvkaek skkkkeeeed eedeedeeee edeededeee ddddd
``` orchestrates both processes by switching among mutually exclusive redox states. Reduced cysteines make HMGB1 a chemoattractant, while a disulfide bond makes it a proinflammatory cytokine and further cysteine oxidation to sulfonates by reactive oxygen species abrogates both activities. The authors show that leukocyte recruitment and activation can be separated. A non-oxidizable HMGB1 mutant in which serines replace all cysteines (3S-HMGB1) does not promote cytokine production but is more effective than wild type HMGB1 in recruiting leukocytes in vivo. BoxA, a HMGB1 inhibitor, interferes with leukocyte recruitment but not with activation. The authors detected the different redox forms of HMGB1 ex vivo within injured muscle. HMGB1 is completely reduced at first and disulfide-bonded later. Thus, HMGB1 orchestrates both key events in sterile inflammation, leukocyte recruitment and their induction to secrete inflammatory cytokines, by adopting mutually exclusive redox states.

In the present invention, the authors have investigated how different redox states of HMGB1 impact its chemotactic activities. Surprisingly, they found that:
- only the fully reduced form of HMGB1, where all 3 cysteines are in the thiol state, can attract motile cells; this form is totally inactive in stimulating cytokine secretion;
- cytokine-stimulating and chemotactic activities of HMGB1 are mutually exclusive;
- terminally oxidized HMGB1 (i.e HMGB1 in which at least one cysteine is oxidized to sulfonate) has no activity either as a chemoattractant or in cytokine stimulation.
- cysteines are required for the cytokine-stimulating activity, but none are required for the chemoattractant function of HMGB1.

In order to study the involvement of individual cysteines in the cytokine-stimulating and chemotactic activities of HMGB1, the authors have replaced them with serine residues and have generated mutants:
1S-HMGB1 (where C23 or C45 or C106 are replaced by a serine),
2S-HMGB1 (where both C23 and C45 or both C45 and C106 are replaced),
3S-HMGB1 (where all three cysteines are replaced).

The activity of the mutants above, have been tested on fibroblasta and macrophages. They all induced fibroblast migration but not cytokines/chemokines expression by macrophages.

Moreover, it has been observed that mutants 2S and 3S showed same chemotactic activity whether exposed to DTT or not (as expected since there is no disulphide bond that can be reduced) and treatment with $H_2O_2$ inhibited cell migration in response to all HMGB1 mutants, with the exception of mutant 3S that does not have a cysteine that can be terminally oxidized. Overall, the results indicate that:

C23-C45 disulphide bond is required for the pro-inflammatory activity but disrupts the chemotactic activity of HMGB1;

Each of C23, C45 and C106 are essential for the pro-inflammatory activity but their conservative substitution with another residue such as serine preserves the chemotactic activity.

Thus, mutant 3S can promote cell recruitment but cannot induce release of pro-inflammatory mediators, even in oxidative conditions and mutant 3S cannot be inactivated by oxidation.

The authors showed that all cysteines must be reduced for chemoattractant activity of HMGB1. Therefore, the cytokine-stimulating and chemotactic activities of HMGB1 are mutually exclusive. When cysteines are oxidized to sulfonates (i.e. terminally oxidized), HMGB1 is inactive both as a chemoattractant and as a pro-inflammatory cytokine. The different redox forms of HMGB1 are detected ex vivo and in vivo in a model of muscle injury. The authors replaced HMGB1 cysteines with serines, and showed that none of the cysteines is essential for the chemotattractant function of HMGB1. The 3S mutant, in which all cysteines are replaced with serines, induces cell recruitment but not cytokine production, and is resistant to inactivation by oxidation. Thus, the present HMGB1 mutants can be used as therapeutic agents to favor tissue regeneration. They are particularly suitable as they can recruit inflammatory cells without activating them to a pro-inflammatory state.

It is therefore an object of the invention an HMGB1 variant characterized in that it is a cell chemoattractant and it does not stimulate cytokine and/or chemokine production from a cell, orthologs, derivatives and fragments thereof.

Preferably the HMGB1 variant or orthologs, derivatives and fragments thereof has at least one cysteine residue is replaced by a different amino acid residue.

Preferably the at least one cysteine residue is replaced by an amino acid residue containing the same number of carbon atoms as cysteine. This includes serine or alanine Preferably at least one cysteine residue is replaced by a serine residue.

Still preferably at least one cysteine residue is located in any one of positions 23, 45 or 106 of SEQ ID No. 1. More preferably the cysteine residue is located in position 106 of SEQ ID No. 1. In a preferred embodiment the HMGB1 variant or orthologs, derivatives and fragments thereof of the invention has at least two cysteine residues that are replaced by different amino acid residues.

Preferably the at least two cysteine residues are each replaced by an amino acid residue containing the same number of carbon atoms as cysteine.

Preferably the at least two cysteine residues are each replaced by serine residues.

Still preferably the cysteine residues are located in any one of positions 23, 45 or 106 of SEQ ID No. 1.

Still preferably the cysteine residues are located at positions 23 and 45 of SEQ ID No. 1.

In a preferred embodiment the HMGB1 variant or orthologs, derivatives and fragments thereof has three cysteine residues that are replaced by different amino acid residues.

Preferably the three cysteine residues are each replaced by an amino acid residue containing the same number of carbon atoms as cysteine.

Still preferably the three cysteine residues are each replaced by serine residues.

It is a further object of the invention a pharmaceutical composition comprising pharmaceutically acceptable diluents and/or excipients and a compound selected in the group comprising:

the HMGB1 variant or orthologs, derivatives and fragments thereof as defined above;

a polynucleotide coding for said HMGB1 variant or orthologs, derivatives and fragments thereof as defined above;

a vector comprising said polynucleotide and a host cell genetically engineered expressing said polypeptide.

It is a further object of the invention a method to promote cell chemotaxis comprising exposing the cell to an effective amount of the HMGB1 variant or orthologs, derivatives and fragments thereof as defined above or to the pharmaceutical composition as defined above.

It is a further object of the invention a method to induce tissue regeneration comprising administering in a subject in need thereof an effective amount of the HMGB1 variant or orthologs, derivatives and fragments thereof as defined above or of the pharmaceutical composition as defined above.

It is a further object of the invention the use of the HMGB1 variant or orthologs, derivatives and fragments thereof of the invention to induce tissue regeneration.

It is a further object of the invention the HMGB1 variant or orthologs, derivatives and fragments thereof as defined above for use in the treatment and/or prevention of a pathology requiring tissue and/or muscle regeneration, in particular recovery from wounds, fractures and physical trauma, ischemia, infarction and recovery thereof of various tissues and/or organs.

The tissue may be soft or hard tissue, including brain.

It is a further object of the invention the HMGB1 variant or orthologs, derivatives and fragments thereof as defined above for use in the prevention and/or repair of muscle and/or bone and/or cartilage damage and for use in the prevention and/or repair of soft tissue such as brain. Preferably the damage is induced by necrosis. Preferably the muscle is skeletal or cardiac muscle. Still preferably the bone damage is consequent to a fracture.

In the present invention a pathology requiring tissue regeneration comprises recovery from wounds, fractures and physical trauma, a pathology or a recovery involving especially but not limited to brain, muscle, bone, tendon, vessels and skin, and ischemia of various tissues and organs, including but not limited to the heart and the brain, or recovery from ischemia of various tissues and organs as indicated above.

The HMGB1 variants of the present invention, obtained by technologies known in the art, are mutant proteins, which differ from the amino acid sequence of the wild type HMGB1 by the mutation of one or more single amino acid. In a very preferred embodiment of the present invention, only one amino acid replacement occurs on the sequence of the native protein. It is, however, encompassed by the subject of the present invention that the native protein can be further optimised by replacement of a plurality, e.g two or more, of amino acid replacements. The variants can therefore differ from the wild type protein sequence by amino acid replacements on 1-10, preferably 1, 2, 3, 4, 5 and 6 different amino acid target positions.

Moreover, the mutants or variants of the invention exhibit chemoattractant function and no cytokine/chemokine stimulating properties.

In the present invention a HMGB1 variant that does not stimulate cytokine and/or chemokine production from a cell is a protein that does not induce cytokines/chemokines expression (for instance analysed by real-time PCR) by cells such as human macrophages. The protein does not induce the production or expression of at least IL-6, IL-8 and TNFα.

In particular, the chemoattractant function in an animal model is prolonged, and therefore more efficacious, because serines cannot be oxidized, and therefore mutant HMGB1 cannot be inactivated by reactive oxygen species. Chemoattractant function was measured as indicated in the method section. Other methods to measure chemotaxis are described in the art and are suitable.

In the context of the present invention, where reference is made to the term "HMGB1 or amino acid sequence of HMGB1", it is referred to both human and non-human HMGB1. In a preferred embodiment of the present invention, the HMGB1 is derived from the wild type of human HMGB1 protein and from the wild type rat HMGB1 protein.

The term "mutation" or "variant" as used in the context of the present invention can be understood as substitution, deletion and/or addition of single amino acid in the target sequence.

Preferably, the mutation of the target sequence in the present invention is a substitution. The substitution can occur with different genetically encoded amino acid or by non-genetically encoded amino acids. Examples for non-genetically encoded amino acids are homocystein, hydroxyproline, omithin, hydroxylysine, citrulline, carnitine, etc.

A further aspect of the present invention is a pharmaceutical composition comprising an effective amount of at least one of the HMGB1 variant or a biologically active fragment thereof as an active ingredient. The pharmaceutical composition of the present invention may be used for diagnostic or for therapeutic applications.

The exact formulation, route of administration and dosage can be chosen by the individual physician in view of the patient's conditions. Administration may be achieved in a single dose or repeated doses at intervals. Dosage amount and interval may be adjusted individually in order to provide the therapeutic effect, which results in amelioration of symptoms or a prolongation of the survival in a patient. The actual amount of composition administered will, of course, be dependent on the subject being treated, on the subject's weight, the severity of the affliction, the manner of administration and the judgement of the prescribing physician. A suitable daily dosage will be between 0.001 to 10 mg/kg, particularly 0.1 to 5 mg/kg. The administration may be carried out by known methods, e.g. by injection, in particular by intravenous, intramuscular, transmucosal, subcutaneous or intraperitoneal injection and/or by oral, topical, nasal, inhalation, aerosol and/or rectal application, etc. The administration may be local or systemic. In addition, the HMGB1 variants object of this invention can be reversibly immobilized and/or adsorbed on the surface and/or inside medical devices or drug release/vehicling systems (microspheres). Medical devices and microspheres can be reversibly loaded with the variants of this invention, through their binding, impregnation and/or adsorption on the surface of the medical device or of the microsphere or on a layer that coats its surface. When the medical device or the microsphere come into contact with biological fluids, the reversibly immobilized variant is released. Therefore, the medical device and the microsphere act as drug-releasing tools that elute the molecule object of this invention in such a way that their release kinetics can be controlled, ensuring controlled or sustained release, as required by the treatment. The methods for coating/impregnating the medical devices and loading microspheres are well known by experts in these technologies.

In the present invention a polypeptide comprising an amino acid sequence having at least 70% identity with the sequence of SEQ ID No. 1 is another embodiment. Said polypeptide is chosen from the group consisting of a homologue, a derivative, an equivalent, and a fragment of a polypeptide.

As used herein, the term "equivalent" will be understood to mean a peptide having at least one of the activities of the instant polypeptide. "Homologue" will be understood as a polypeptide exhibiting certain modifications compared with the natural polypeptide. These modifications can be a deletion, a truncation, an extension, a chimeric fusion, and/or a mutation. Among equivalent polypeptides, those who display more than 80% homology are preferred.

"Derivative" refers to any polypeptides, eventually mutated, truncated, and/or extended, which have been chemically modified or contain unusual amino acids. A preferred derivative is a derivative in which the acidic tail (last 30 amino acids of HMGB1) is deleted.

As used herein, the term "polypeptide" refers to a molecular chain of amino acids having chemotaxis properties but which does not stimulate cytokine and/or chemokine production from a cell. This polypeptide, if required, can be modified in vitro and/or in vivo, for example by glycosylation, myristoylation, amidation, carboxylation or phosphorylation, and may be obtained, for example, by synthetic or recombinant techniques known in the art.

As used herein, the term "orthologs" refers to proteins in different species than the proteins SEQ ID NO.1 in *Homo sapiens* that evolved from a common ancestral gene by speciation. As an example of such orthologs, one can cite the proteins corresponding to HMGB1 in *Mus musculus, Rattus norvegicus Gallus gallus, Xenopus laevis* and *Danio rerio*.

As used herein, the term "derivatives" refers to polypeptides having a percentage of identity of at least 75% with SEQ ID NO. 1, or ortholog thereof, preferably of at least 85%, as an example of at least 90%, and more preferably of at least 95%.

As used herein "fragments" refers to polypeptides having a length of at least 25 amino acids, preferably at least 50 amino acids, as an example at least 75 or 85 amino acids, and more preferably of at least 100 amino acids. In the present invention all fragments and derivatives possess chemoattractant properties but do not stimulate or induce cytokine and/or chemokyne production, in particular IL-6, IL-8 and TNFα.

As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest.

Sequences comparison between two amino acids sequences are usually realized by comparing these sequences that have been previously align according to the best alignment; this comparison is realized on segments of comparison in order to identify and compared the local regions of similarity. The best sequences alignment to perform comparison can be realized, beside by a manual way, by using the global homology algorithm developed by SMITH and WATERMAN (Ad. App. Math., vol. 2, p:482, 1981), by using the local homology algorithm developed by NEDDLEMAN and WUNSCH (J. MoI. Biol, vol. 48, p:443, 1970), by using the method of similarities developed by PEARSON and LIPMAN (Proc. Natl. Acd. Sci. USA, vol. 85, p:2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C, Nucleic Acids Research, vol. 32, p:1792, 2004). To get the best local alignment, one can preferably used BLAST software, with the BLOSUM 62 matrix, or the PAM 30 matrix. The identity percentage between two sequences of amino acids is determined by comparing these two sequences optimally aligned, the amino acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

As used herein, the term "polynucleotide" refers to RNA or DNA, preferably to DNA. Said DNA may be double-stranded or single-stranded.

Preferably, the polynucleotide comprises the sequence of 1S-HMGB1, 2S-HMGB1, 3S-HMGB1. Preferably, the polynucleotide comprises a sequence which encodes the sequence of 1S-HMGB1, 2S-HMGB1, 3S-HMGB1.

The polynucleotide of the invention may also include the coding sequence of the polypeptide defined previously, additional coding sequence such as leader sequence or a proprotein sequence, and/or additional non-coding sequence, such as introns or 5' and/or 3' UTR sequences.

As used herein, the term "vector" refers to an expression vector, and may be for example in the form of a plasmid, a viral particle, a phage, etc. Such vectors may include bacterial plasmids, phage DNA, baculovirus, yeast plasmids, vectors derived from combinations of plasmids and phage DNA, viral DNA such as vaccinia, adenovirus, fowl pox virus, and pseudorabies. Large numbers of suitable vectors are known to those of skill in the art and are commercially available. The following vectors are provided by way of example. Bacterial: pQE70, pQE60, pQE-9 (QIAGEN), pbs, pDIO, phagescript, psiX174, pbluescript SK, pbsks, pNH8A, pNH1[beta]a, pNH18A, pNH46A (STRATAGENE), ptrc99a, pKK223-3, pKK233-3, pDR540, pRIT5 (PHARMACIA). Eukaryotic: pWLNEO, pSV2CAT, pOG44, pXT1, pSG (STRATAGENE), pSVK3, pBPV, pMSG, pSVL (PHARMACIA). However, any other vector may be used as long as it is replicable and viable in the host. The polynucleotide sequence, preferably the DNA sequence in the vector is operatively linked to an appropriate expression control sequence(s) (promoter) to direct mRNA synthesis. As representative examples of such promoters, one can mentioned prokaryotic or eukaryotic promoters such as CMV immediate early, HSV thymidine kinase, early and late SV40, LTRs from retrovirus, and mouse metallothionein-I. The expression vector also contains a ribosome binding site for translation initiation and a transcription vector. The vector may also include appropriate sequences for amplifying expression.

In addition, the vectors preferably contain one or more selectable marker genes to provide a phenotypic trait for selection of transformed host cells such as dihydro folate reductase or neomycin resistance for eukaryotic cell culture, or such as tetracycline or ampicillin resistance in E. coli.

As used herein, the term "host cell genetically engineered" relates to host cells which have been transduced, transformed or transfected with the polynucleotide or with the vector described previously.

As representative examples of appropriate host cells, one can cites bacterial cells, such as E. coli, Streptomyces, Salmonella typhimurium, fungal cells such as yeast, insect cells such as Sf9, animal cells such as CHO or COS, plant cells, etc. The selection of an appropriate host is deemed to be within the scope of those skilled in the art from the teachings herein.

Preferably, said host cell is an animal cell, and most preferably a human cell.

The introduction of the polynucleotide or of the vector described previously into the host cell can be effected by method well known from one of skill in the art such as calcium phosphate transfection, DEAE-Dextran mediated transfection, or electroporation.

The composition of the invention may comprise one or more additives (e.g., stabilizers, preservatives).

See, generally, Ullmann's Encyclopedia of Industrial Chemistry, 6th Ed. (various editors, 1989-1998, Marcel Dekker).

According to the present invention, an "effective amount" of a composition is one which is sufficient to achieve a desired biological effect, in this case inducing and/or promoting chemotaxis or inducing tissue regeneration. It is understood that the effective dosage will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges. However, the preferred dosage can be tailored to the individual subject, as is understood and determinable by one of skill in the art, without undue experimentation. Said polypeptide, polynucleotide, vector, and host cell are as described previously.

BRIEF DESCRIPTION OF THE DRAWINGS

The invention will be now illustrated by means of non-limiting examples referring to the following figures.

FIG. 1. Characterization of HMGB1 redox states.

FIG. 2. The cytokine-stimulating and chemoattractant activities of HMGB1 are mutually exclusive.

FIG. 3. BoxA and monoclonal antibody DPH1.1 prevent HMGB1-induced cell migration but not cytokine expression.

FIG. 4. HMGB1 cysteines are essential to promote cytokine/chemokine production, but not for chemotaxis.

FIG. 5. Oxidation modulates the activities of HMGB1 in vivo. (FIG. 5C) Alternatively, air pouches were injected with 200 μl of PBS containing or not 1 or 10 nmol HMGB1 (wt or 3S) (FIG. 5C) or with 1 nmol HMGB1 (wt or 3S) in absence or presence of N-acetylcysteine (NAC) (100 nmol/g) (FIG. 5D). After 6 hrs cells were collected from the air pouches, stained with anti-Ly6C and anti-CD11b antibodies and analyzed by flow cytometry (WBCs, White Blood Cells) (*, P<0.05; , P<0.01; *, P<0.001, ANOVA plus Dunnett's posttest).

FIG. 6. HMGB1 induces the recruitment of macrophages M2 and satellite cells in vivo in a model of acute muscle injury. Muscle injury was performed on the tibialis anterior (TA) of 8-weeks-old C57BL/6 by injecting 50 μl of 15 μM cardiotoxin (CTX) in presence or not of 150 μg HMGB1 (wt or 3S) (three animals per group). Mice were sacrificed 2 or 5 days after CTX injection, and the TA muscles were dissected and frozen in liquid N2-cooled isopentane. (FIG. 6A). Immunofluorescence staining of satellite cells (Pax 7, green) on sections of TA muscles 5 days after the intramuscular injection of cardiotoxin and HMGB1 (wt or 3S). (FIG. 6B).

FIG. 9. HMGB1 mutants induce cell migration but not cytokine/chemokine production.

DETAILED DESCRIPTION OF THE INVENTION

Figure 1A:
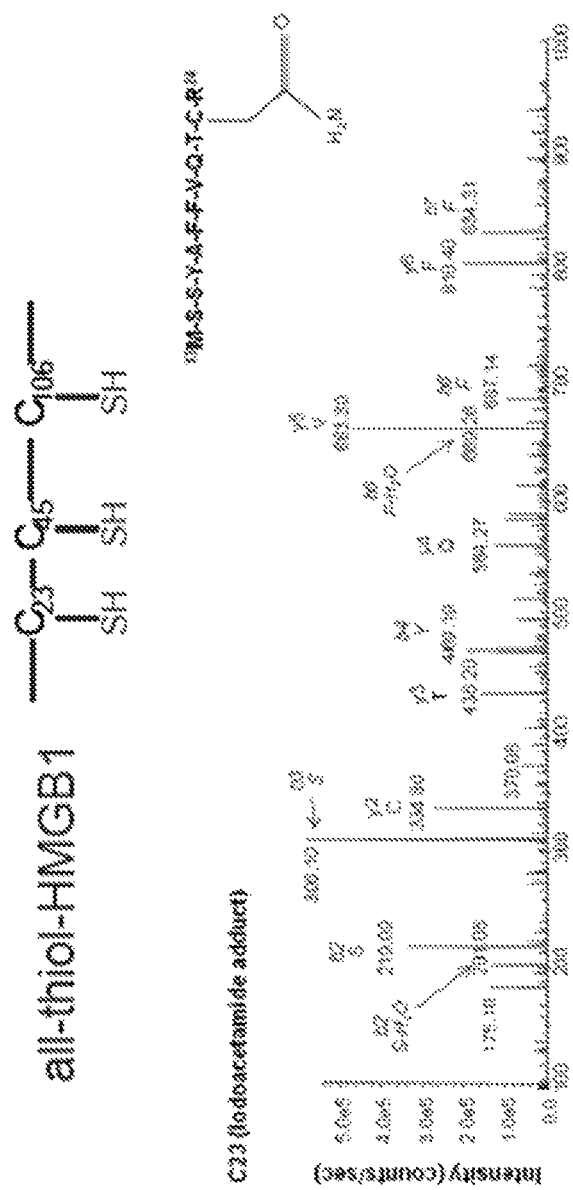
(FIGS. 1A-1E) Mass spectrometric characterization of HMGB1 purified with DTT (1A-1C) or without DTT (1D-1E). Characterization of C23: MS-MS trace of the peptide containing amino acids 13-24, with a iodoacetamide adduct indicating reduced C23 (1A-1C) or with a NEM adduct following DTT reduction of a disulfide bond (1D-1E). Characterization of C45: MS-MS trace of the peptide containing amino acids 45-48, with a iodoacetamide adduct indicating reduced C45 (1A-1C) or with a NEM adduct following DTT reduction of a disulfide bond (1D-1E). Characterization of C106: MS-MS trace of the peptide containing amino acids 97-112 with a iodoacetamide adduct indicating reduced C106 (1A-1C); the MS-MS trace from disulfide-HMGB1 was identical and is not shown.

Materials and Methods
Reagents.

Human macrophage colony-stimulating-factor (M-CSF) and granulocyte macrophage colony-stimulating-factor (GM-CSF) were purchased from R&D Systems Inc. (Minneapolis, Minn., USA); DMEM, X-Vivo medium, Phosphate Buffered Saline (PBS), glutamine and penicillin/streptomycin from Lonza (Walkersville, Md., USA); Fetal Bovine Serum (FBS) from GIBCO (Karlsruhe, Germany); hydrogen peroxide (30%) from BDH Chemicals Ltd. (Poole, UK). Polyclonal rabbit anti-human HMGB1 antibody was purchased from Abcam (ab18256, Cambridge, U.K.) and the monoclonal mouse anti-HMGB1 DPH1.1 antibody was from HMGBiotech srl. (HM901, Milan, Italy). F(ab')$_2$ fragments were generated from the DPH1.1 antibody using the Pierce mouse IgG1 Fab and F(ab')$_2$ micropreparation kit (Thermo Fischer Scientific, Rockford, Ill., USA) following the manufacturer's instructions. Cardiotoxin (C9759) and all other chemicals and materials were purchased from Sigma-Aldrich (St. Louis, Mo., USA). CXCL12 was synthesized using tBoc solid-phase chemistry (Clark-Lewis et al., 1997).

Mice and Treatments.

Eight weeks old C57BL/6 mice were purchased from The Jackson Laboratory (Bar Harbor, Me.). Sterile injury was induced by injection of 50 µl of 15 µM cardiotoxin (CTX) in the tibialis anterior muscle. After the indicated times, muscles were isolated from mice and incubated for 2 h at 37° C. in PBS containing protease inhibitors and Collagenase D (Roche, Mannhein, Germany); samples were centrifuged and supernatants were preserved at −80° C. before western blotting. Air pouches were established in 8 weeks old male C57BL/6 mice by dorsal subcutaneous injection of 5 and 3 ml of air at day 0 and day 3, respectively. At day 6, the air pouches were injected with 200 µl of PBS containing 10 pmol CXCL12, 300 pmol HMGB1 (wt or 3S) or CXCL12 10 pmol+HMGB1 300 pmol (wt or 3S) or with 200 µl of PBS containing 0, 1 or 10 nmol HMGB1 (wt or 3S). After 6 hrs cells were collected from the air pouches, stained with anti-Ly6C (BD, 557359) and anti-CD11b (Biolegend, 101216) antibodies and analyzed by flow cytometry.

Alternatively muscle injury was performed on the tibialis anterior (TA) of 8-weeks-old C57BL/6 by injecting 50 µl of 15 µM cardiotoxin (CTX) in presence or not of 150 µg HMGB1 (wt or 3S) (three animals per group). Mice were sacrificed 2 or 5 days after CTX injection, and the TA muscles were dissected and frozen in liquid N2-cooled isopentane. This model reflects injury by necrosis.

Animal experimentation was carried out in Istituto Scientifico San Raffaele as approved by "Comitato Istituzionale per la Buona Sperimetazione Animale della Fondazione San Raffaele del Monte Tabor" on Sep. 19, 2011.

Cells.

The mouse 3T3 fibroblast cell line, the THP-1 human acute monocytic leukemia cell line and the mouse myoblast cell line C2C12 were purchased from American Type Culture Collection (Rockville, Md., USA) and cultured in DMEM supplemented with 10% FBS, 2 mM glutamine, 100 units/ml penicillin and 100 µg/ml streptomycin. Peripheral blood mononuclear cells (PBMCs) were isolated from buffy coats of donor blood (Hospital of Magenta, Italy) by Ficoll gradient centrifugation (Lymphoprep, AXIS-SHIELD). CD14+ monocytes were isolated by positive immunoselection (CD14 MicroBeads, Miltenyi Biotec, Germany) according to the manufacturer's instructions, and differentiated into macrophages using X-Vivo medium supplemented with 1% heat inactivated human serum, GM-CSF and M-CSF.

Isolation of HMGB1.

HMGB1 was isolated by immunoprecipitation (IP) from THP-1 samples as previously described (7). Proteins were then separated by non-reducing SDS-PAGE, and protein bands corresponding to the molecular weight of HMGB1 were excised and subjected to tryptic digestion. The resulting peptides were characterized by liquid chromatography and tandem mass spectrometry (LC-MS/MS) as described previously (7). Individual peptide fragmentation to produce b and y ions was utilized to determine the amino acid sequence and confirm the presence of specific modifications.

Production of Recombinant Wt and Mutant HMGB1 Proteins.

The wild type HMGB1 used in the experiments is the rat protein (MGKGDPKKPR GKMSSYAFFV QTCREEH-KKK HPDASVNFSE FSKKCSERWK TMSAKEKGKF EDMAKADKAR YEREMKTYIP PKGETKKKFK DPNAPKRPPS AFFLFCSEYR PKIKGEHPGL SIGD-VAKKLG EMWNNTAADD KQPYEKKAAK LKEKYEK-DIA AYRAKGKPDA AKKGVVKAEK SKKKKEEEDD EEDEEDEEEE EEEEDEDEEE DDDDE SEQ ID No. 2), with no tags or additional amino acids, expressed in E. coli and purified to homogeneity as previously described (6). The plasmid encoding wild-type HMGB1 was freshly transformed into protease-deficient E. coli strain BL21 (Novagen) and incubated in 2-YT medium. Protein expression was induced at 23° C. by addition of 1 mM IPTG overnight. Harvested cells were resuspended in 50 mM Tris-HCl pH 8.0, 20 mM EDTA, 0.5 mM PMSF (containing or not 1 mM DTT as appropriate) and sonicated at 4° C. NaCl was added to a final concentration of 0.5 M and the cell debris were discarded. Crystalline ammonium sulfate (0.39 g per ml) was added to the supernatant, and the protein precipitate was discarded. The supernatant was purified on a HiLoad 26/10 Phenyl Sepharose High Performance column (GE Healthcare) connected to a FPLC system (Akta Purifier, GE Healthcare). Proteins were eluted at RT by a continuous descending gradient of ammonium sulfate (39% to 0%) in 20 mM HEPES pH 7.9, 0.2 mM PMSF, 0.2 mM EDTA pH 8 (plus 0.5 mM DTT where appropriate). Fractions containing HMGB1 (identified by Coomassie staining after SDS-PAGE) were pooled, dialyzed overnight against 50 mM HEPES pH 7.9, 0.2 mM PMSF, 20 mM NaCl (plus 0.5 mM DTT where appropriate), and loaded on a Hi-trap Q column (GE Healthcare). Proteins were eluted with an increasing ionic-strength buffer (from 20 mM to 1 M NaCl) in 50 mM HEPES pH 7.9, 0.2 mM PMSF, 1 M NaCl (plus 0.5 mM DTT where appropriate). The purity and integrity of purified HMGB1 was verified by Coomassie blue staining after SDS-PAGE. The authors also tested HMGB1 before and after digestion with DNAse I (100 U/ml, Invitrogen), and the authors observed no difference in activity. The protein was stored at −80° C. Buffers were always degassed before use. E106 (C106 was replaced by a glutamic acid), C23S, C45S, 1S-HMGB1 (C106S), 2S-HMGB1 (C23-C45S), C45-106S and 3S-HMGB1 mutants were generated using the QuikChange XL Site-Directed Mutagenesis kit according to the manufacturer's instructions (Stratagene), and were checked by sequencing. Mutant proteins were expressed, purified and quality-controlled as wild-type (wt) HMGB1.

BoxA from HMGB1 is produced in $E.\ coli$ from an expression plasmid coding for the unmodified mammalian sequence, which is totally identical in human and mouse (Müller et al. Thermodynamics of HMGB1 interaction with duplex DNA. Biochemistry 2001, 40: 10254-61). It has the sequence:

```
                                            (SEQ ID No. 3)
MGKGDPKKPR GKMSSYAFFV QTCREEHKKK HPDASVNFSE

FSKKCSERWK TMSAKEKGKF EDMAKADKAR YEREMKTYIP

PKGETKKKF.
```

Box A was expressed, purified and quality-controlled as wild-type (wt) HMGB1.

LPS in HMGB1 Preparations.

Contaminating LPS was removed from protein preparations by Triton X-114 extraction (6). The authors measured LPS in HMGB1 samples from all preparations using the Cambrex Limulus Amoebocyte Assay QCL-1000 (Lonza), before and after terminal digestion with trypsin (therefore excluding any interference of HMGB1 with the assay). LPS content was always below 0.4 ng/mg protein; this amount of LPS is totally ineffective in the authors' assays when administered alone (unpublished data). Experiments were also performed in presence of Polymyxin B (10 µg/ml) to neutralize the biological activity of LPS, even though it was not found in HMGB1 preparations.

Preparation of Reduced or Terminally Oxidized HMGB1.

Wt or mutants HMGB1 were exposed to either $H_2O_2$ (100 mM) or DTT (5 mM) for 1 hour and dialyzed prior to the addition to cells or other analyses.

Mass-Spectrometric Characterization of the Cysteine Oxidation Status of Recombinant or Circulating HMGB1.

Reduced cysteine residues within HMGB1, either recombinant or obtained from THP-1 cells, were characterized by thiol-specific alkylation with 50 mM iodoacetamide for 30 min. Alkylation with iodoacetamide yields a mass-shift of 57 amu (atomic mass unit). Following the incubation, recombinant HMGB1 preparations were precipitated with ice-cold methanol (MeOH). The pellet was recovered after centrifuging at 14,000 g at 4° C. for 10 min. The presence of SOH residues in cysteines was investigated with a 20 min incubation with 0.1 mM dimedone (5,5-dimethyl-1,3-cyclohexanedione). $SO_2H$ and $SO_3H$ oxidative modifications were sought by looking for mass increases of 32 and 48 amu respectively on each particular cysteine residue. After the first alkylation step, remaining cysteine residues engaged in a disulfide bond were reduced with 1 mM DTT at 4° C. for 15 min. Newly reduced cysteines were then alkylated with 50 mM N-ethylmalemide (NEM) for 5 min on ice, which yields a mass shift of 125 amu. HMGB1 was isolated by immunoprecipitation (IP) from THP-1 samples as previously described (7). Proteins were then separated by non-reducing SDS-PAGE, and protein bands corresponding to the molecular weight of HMGB1 were excised and subjected to tryptic digestion. The resulting peptides were characterized by liquid chromatography and tandem mass spectrometry (LC-MS/MS) as described previously (7). Individual peptide fragmentation to produce b and y ions was utilized to determine the amino acid sequence and confirm the presence of specific modifications.

Western Blotting.

Total protein content in muscle samples from control or CTX-treated mice was determined using the Protein Assay Dye Reagent (Bio-Rad Laboratories Ltd, Hemel Hemstead, U.K.). Equivalent amounts of proteins were loaded on gels. For western blotting, protein samples were separated on 12% SDS-PA gels and transferred on nitrocellulose membranes, which were blocked with 5% skim milk in Tris-buffered saline (pH 7.0) containing 0.1% Tween 20 (TBS-T). Blocked membranes were probed with rabbit anti-HMGB1 (1:1000, Abcam, ab18256) in TBS-T plus 5% milk overnight at 4° C., washed several times with TBS-T, and incubated for 1 h with anti-rabbit peroxidase-conjugated antibody (1:10,000). Western blots were visualised using an enhanced chemiluminescence kit according to the manufacturer's instructions (GE Healthcare, Little Chalfont, UK).

Living Cell Microscopy.

Immortalized fibroblasts were derived from knock-in mice where the endogenous p65 gene was replaced by GFP-p65 (8). Cells were cultured on special chambered glass slides for confocal microscopy (Lab-Tek) in DMEM supplemented with 10% FCS. Cells were serum-starved for 16 h and then stimulated with 80 nM HMGB1 produced with or without DTT as indicated. Subsequently, living cells were imaged using a Leica TCS SP5 AOBS confocal microscope equipped with a ArgonPlus Ar-ion laser (220 mW nominal power; power measured at the objective: 11.4 mW for the 488 nm), a HCX PL Apo CS 63× oil immersion objective/1.4 NA, and a humidified thermostatic chamber (37° C. and 5% CO2) as previously described (9); time lapse images were taken and 30 min time-point images are shown.

Chemotaxis Assays.

For fibroblast chemotaxis, modified Boyden chambers were used with filters (8 µm pores, Neuro Probe) coated with fibronectin (50 µg/ml, Roche). Fifty thousand cells in 200 µl were added to the upper chamber; HMGB1 or mutants were added to the lower chamber, and then cells were left to migrate for 3 h at 37° C. Non-migrating cells were removed with a cotton swab, and migrated cells were fixed with ethanol and stained with Giemsa. All assays were done in triplicate and migrated cells were counted in 10 random fields/filter.

For monocytes, chemotaxis was assayed in 48-well Boyden microchambers (Neuro Probe, Cabin John, Md.) as previously described (Uguccioni et al., 1995). Briefly, freshly isolated monocytes ($5 \times 10^4$) were diluted in RPMI 1640 supplemented with 20 mM HEPES, pH 7.4, 1% pasteurized plasma protein solution (5% PPL SRK) and chemoattractants were diluted in the same buffer supplemented with Polymyxin (10 µg/ml). Cells were then added to the upper wells. After 90 min of incubation, the membrane was removed, washed on the upper side with PBS, fixed, and stained. All assays were done in triplicate, and for each well the migrated cells were counted at 1000-fold magnification in randomly selected fields.

Hybrid ELISA.

The heterocomplex between CXCL12 and HMGB1 (all-thiol or disulfide-HMGB1) was detected by a hybrid ELISA. The plates (Costar 3596, Corning Incorporated, NY, USA) were coated overnight with an anti-CXCL12 capture antibody (human CXCL12/SDF-1 DuoSet ELISA, R&D systems, MN, USA), then blocked with diluent solution (1% BSA in PBS) for 3 hours. CXCL12 and HMGB1 (2:1 stoichiometric ratio) were preincubated at 37° C. for 15 minutes in agitation, in order to promote the formation of the heterocomplex. The samples were distributed in the wells in diluent solution and incubated for 2 hours. After 2 hours of incubation with an Enzyme-conjugated anti-HMGB1 antibody (HMGB1 ELISA, IBL International, Germany), the reaction was visualized by the addition of the Substrate solution and stopped with Stop solution (HMGB1 ELISA, IBL International, Germany). Optical density was measured at 450 nm. All the procedure was performed at room temperature and 4 washes were repeated before each step of the procedure using 0.1% Tween 20 in PBS.

Quantitative Real-Time Polymerase Chain Reaction.

Total RNAs were isolated using the Illustra RNAspin Mini kit (GE Healthcare), and complementary DNA (cDNA) was obtained by retro-transcription with Oligo(dT) primers (Invitrogen, Carlsbad, Calif., USA) and SuperScript II Reverse Transcriptase (Invitrogen) following the manufacturers' instructions. Quantitative real-time PCR was then performed in duplicates using LightCycler480 (Roche Molecular Diagnostics), SYBR Green I master mix and the following primers:

```
β-actin:
                                       (SEQ ID No. 4)
5'-TGACGGGGTCACCCACACTGTGCCC-3',
and (SEQ ID No. 5)
5'-CTAGAAGCATTGCGGTGGAC GATGG-3';

TNF-α:
                                       (SEQ ID No. 6)
5'-AGCCCATGTTGTAGCAAACC-3'
and (SEQ ID No. 7)
5'-AGGACCTGGGAGTAGATGAGG-3';

IL-6:
                                       (SEQ ID No. 8)
5'-TACCCCCAGGAGAAGATTCC-3'
and (SEQ ID No. 9)
5'-TTTTCACCAGGCAAGTCTCC-3;

IL-8:
                                       (SEQ ID No. 10)
5'-TGCCAAGGAGTGCTAAAG-3'
and (SEQ ID No. 11)
5'-CTCCACAACCCTCTGCAC-3';

MIP-2:
                                       (SEQ ID No. 12)
5'-TGCCAGTGCTTGCAGAC-3'
and (SEQ ID No. 13)
5'-TCTTAACCATGGGCGATGC-3'.
```

The ΔCt method was used for quantification, and the β-actin gene was used for normalization.

Immunohistochemical and Immunofluorescence Analysis.

Immunohistochemical and immunofluorescence (IF) analyses were performed on frozen tibialis anterior muscles (TA) sections from control and treated mice using the following antibodies: CD163 (Santa Cruz Biotechnology, 1:100), Pax7 (DSHB, 1:20).

Sections of TA muscles were air-dried for 30 min and fixed in acetone at −20° C. or paraformaldehyde 4% at room temperature for 10 min. IF sections were both blocked for 1 h with 5% bovine serum albumin (BSA) and 0.1% Triton diluted in PBS 1×. Sections were then incubated with antibodies over night at 4° C. Sections were washed with PBS and then incubated with appropriated secondary antibodies (Alexafluor, 1:500) for 1 h at room temperature. Nuclei were revealed by counterstaining with hematoxylin or Hoechst.

For histological analysis, serial muscle sections were obtained and stained in Hematoxilin & Eosin (H&E) following standard procedures. Necrotic cells were identified by hypereosinophilia, thinning and waviness and presence of many nuclei while regenerating fibers were distinguished based on the central localisation of their nuclei.

For each experiments twenty random images for each muscle were taken at 20 or 40× magnification using a Nikon Eclipse E600 microscope (Nikon Instruments Europe) with a Digital camera DXm1200 (Nikon, Nikon Instruments Europe) and analyzed using a digitized imaging systems (ImageJ 1.38 National Institute of Health) and Adobe Photoshop CS4 program.

Statistical Analysis.

Statistical analysis was performed using GraphPad Prism software. Differences between treatment groups were determined by Student's t or Mann-Whitney U tests; p values less than 0.05 were considered statistically significant. For experiments with multiple doses and air pouch experiments ANOVA was carried out, followed by Dunnett's post-test.

Results

Recombinant HMGB1 can be Reversibly Oxidized and Reduced

Figure 1B:
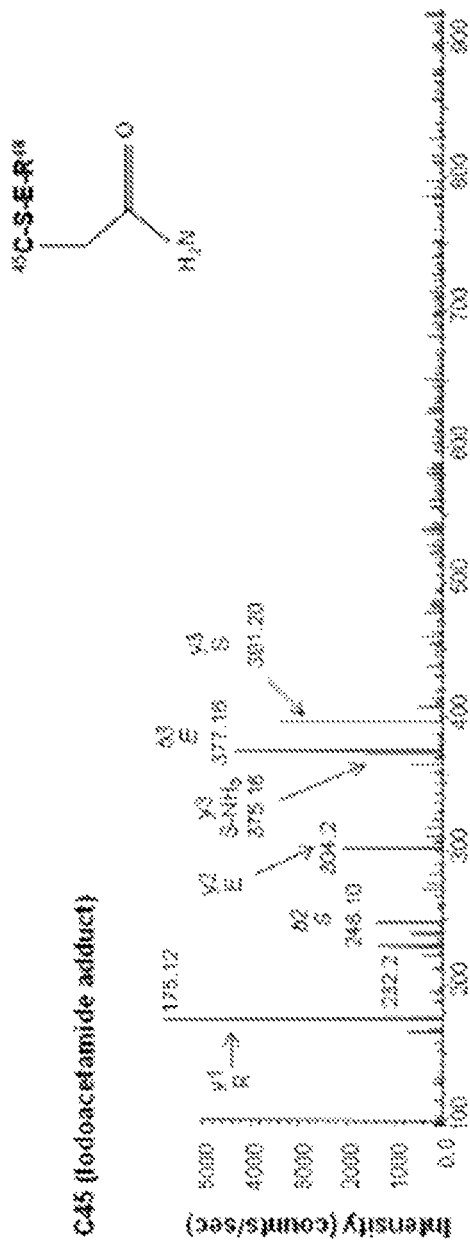
Figure 1C:
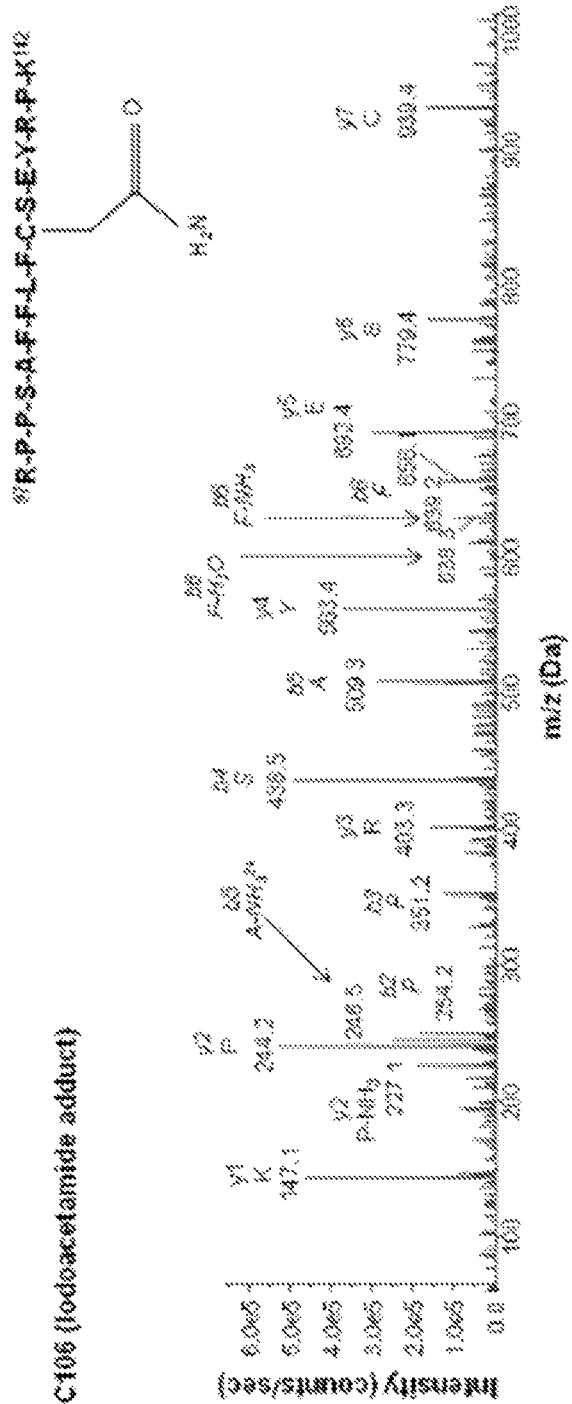
Figure 1D:
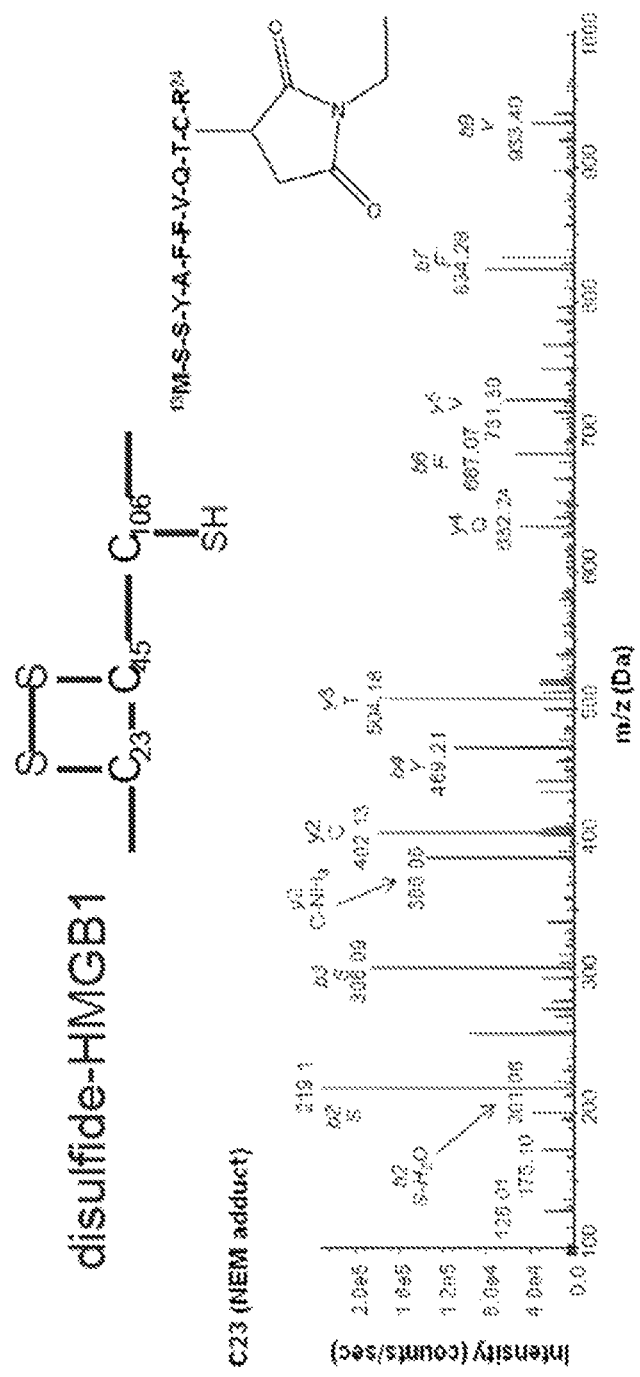
Figure 1E:
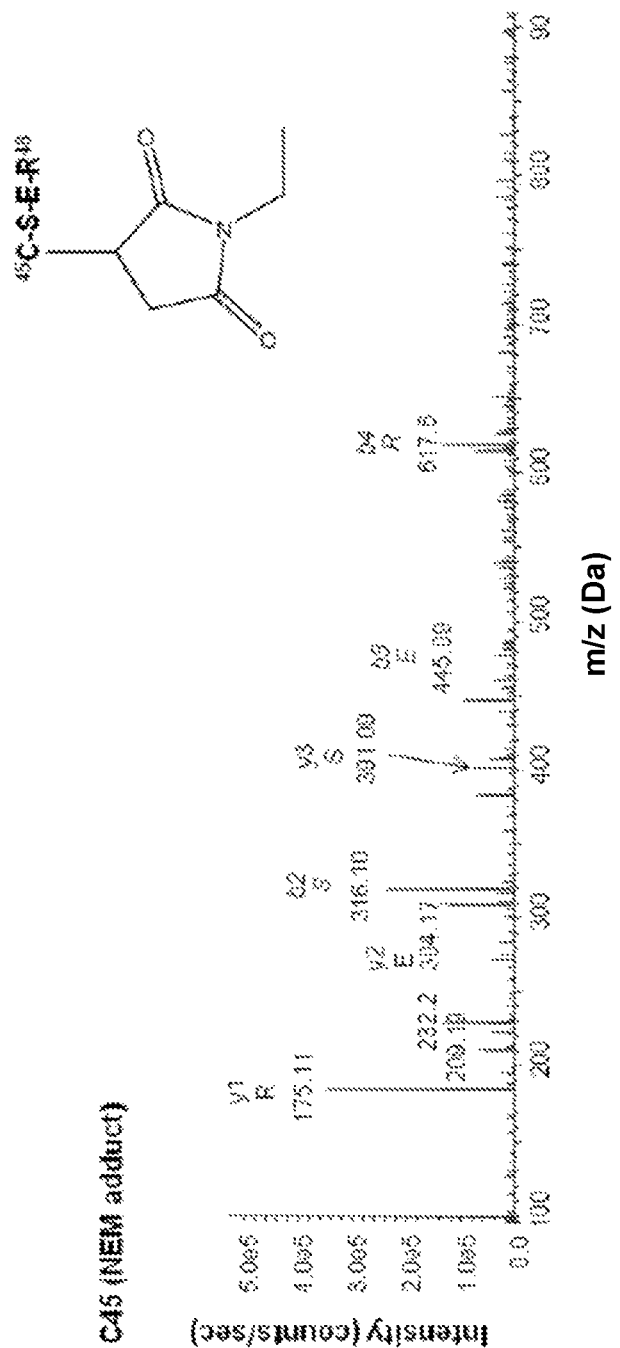

All previous studies by the authors' group relied on bacterially produced full-length HMGB1 protein, purified in the presence of dithiothreitol (DTT) added to degassed buffers (6). Since HMGB1 can exist in different redox forms, the authors compared different batches of HMGB1 purified in the presence or absence of DTT. The authors specifically excluded any LPS contamination (see Materials and Methods). To characterize the redox state of HMGB1, the authors alkylated reduced cysteines with iodoacetamide, then reduced disulfide bonds with DTT and reacted them with N-ethylmaleimide (NEM); the authors then performed tryptic digestion and liquid chromatography tandem mass spectrometric analysis (LC-MS/MS). HMGB1 purified with DTT gave rise to peptides of 1569.1 (doubly-charged ion $784.5^{2+}$), 622.6 (doubly-charged ion $311.3^{2+}$) and 2070.0 Da (triply-charged ion $690.0^{3+}$). MS/MS revealed an iodoacetamide adduct on all cysteines, indicative of a thiol side chain (FIG. 1A-1C); the authors will henceforth call this form all-thiol-HMGB1. A similar analysis of HMGB1 produced in the absence of DTT revealed NEM adducts on C23 and C45, indicating that they formed a disulfide bond (FIG. 1D-1E); C106 was reduced also in this form of HMGB1 (henceforth, disulfide-HMGB1). No SOH, $SO_2H$ or $SO_3H$ modification of cysteines was identified within these forms of HMGB1.

Figure 1F:
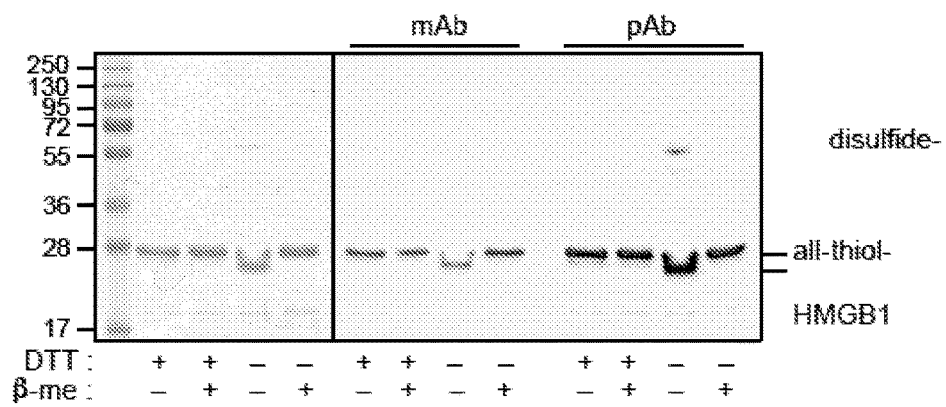
(FIG. 1F) Electrophoretic mobility of recombinant HMGB1 prepared in the presence (+DTT) or absence of DTT (−DTT). Samples were heated in the presence (+) or absence (−) of 350 mM β-mercaptoethanol (β-me), loaded onto a 12% SDS-PA gel and revealed by Coomassie staining (left panel) or by western blotting using a monoclonal (mAb) or a polyclonal antibody (pAb) against HMGB1 (right panel).

The presence of disulfide bonds is often associated with an increased electrophoretic mobility in non-reducing conditions, due to a more compact folding of the polypeptide chain. All-thiol-HMGB1 migrated as a single band with an apparent mw of 28 kDa, both in reducing and non-reducing conditions. In contrast, disulfide-HMGB1 migrated in non-reducing conditions as a single band of 26 kDa and shifted in reducing conditions to the same 28 kDa position as all-thiol-HMGB1 (FIG. 1F). Monoclonal or polyclonal antibodies against HMGB1 recognized both forms of HMGB1 (FIG. 1F). Disulfide-HMGB1 was readily shifted to the all-thiol-HMGB1 electrophoretic pattern after 5 min exposure to 5 mM DTT; conversely, the authors occasionally detected the formation of disulfide-HMGB1 after dilution in air-equilibrated buffers lacking reducing agents. This indicates that all-thiol- and disulfide-HMGB1 forms are readily interconverted in the presence of electron donors (DTT) or acceptors (oxygen).

Figure 1G:
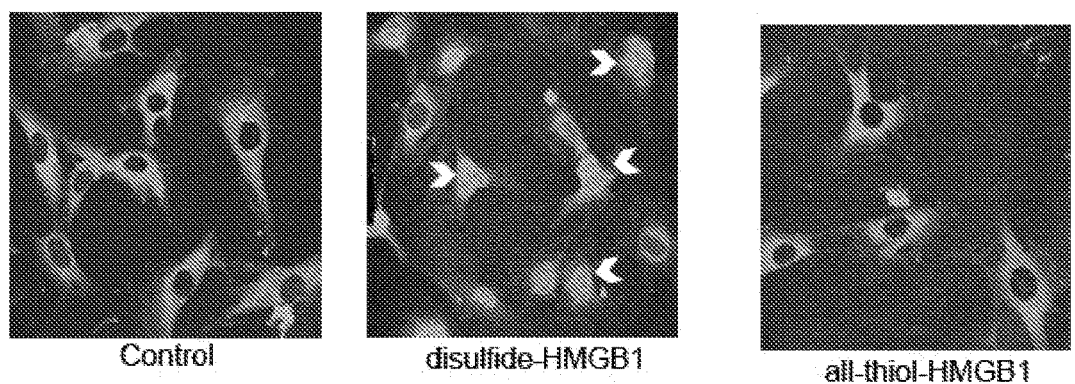
(FIG. 1G) Nuclear translocation of p65-GFP (indicated with white arrows) was visualized by confocal microscopy in living murine embryonic fibroblasts exposed for 30 min to 80 nM disulfide- or all-thiol HMGB1. Data are representative of three independent experiments.
Figure 1H:
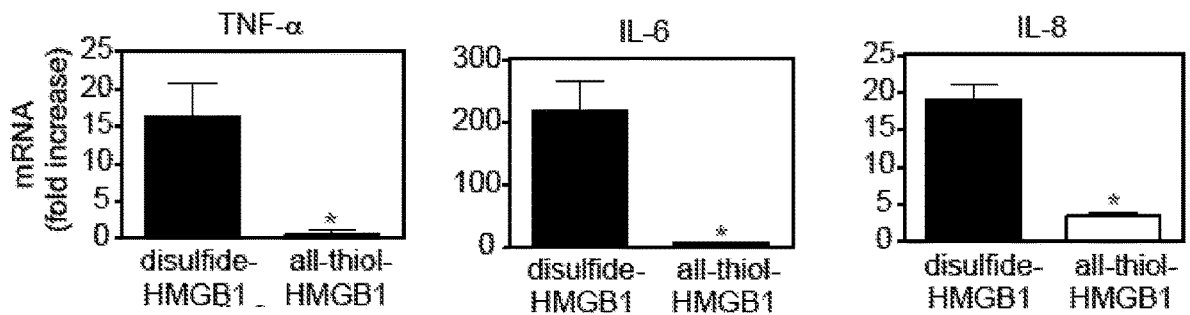
(FIG. 1H) Human macrophages were exposed for 4 hours to 0.4 μM of disulfide- or all-thiol-HMGB1. The levels of TNF-α, IL-6 and IL-8 mRNAs were measured by real-time PCR and expressed as fold increase compared to unstimulated macrophages (*, P<0.05, t test). Error bars represent standard deviation. Data are representative of 3 experiments performed with macrophages from unrelated healthy individuals.
Figure 2A:
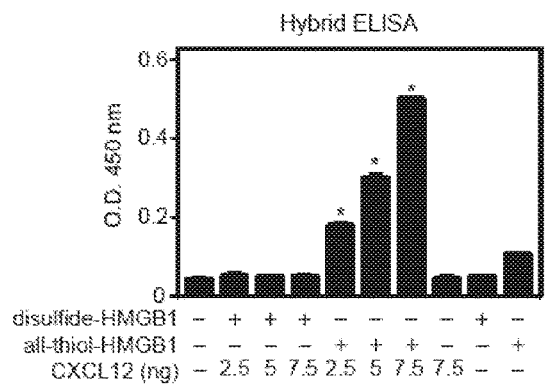
(FIG. 2A) HMGB1/CXCL12 heterocomplex detected by hybrid ELISA. All-thiol- or disulfide-HMGB1 (7.5 ng) were pre-incubated with the indicated amount CXCL12 at 37° C. for 15 minutes. The formation of the heterocomplex was detected by hybrid ELISA (an anti-CXCL12 capture antibody and an anti-HMGB1 detection antibody). Results are expressed as absorbance at 450 nm (*, P<0.05, ANOVA).
Figure 2B:
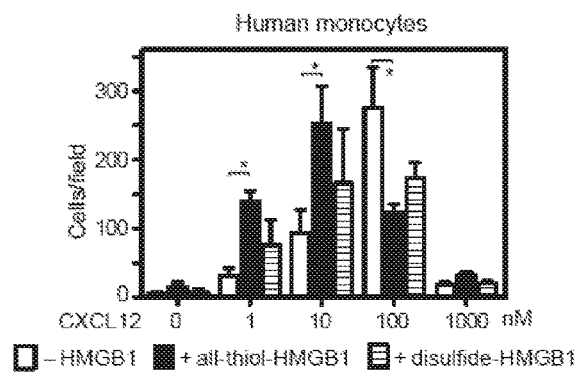
(FIG. 2B) Human monocyte migration in response to increasing concentrations of CXCL12 in the presence or absence of 300 nM all-thiol- or disulfide-HMGB1 (*, P<0.01 vs. CXCL12 alone; 2-way ANOVA).

The Cytokine-Stimulating and Chemoattractant Activities of HMGB1 are Mutually Exclusive Recently, (4,5) showed that disulfide-HMGB1 has cytokine-stimulating activity that is lost after reduction with DTT. The authors confirmed that disulfide-HMGB1 induces activation of the NF-κB pathway (FIG. 1G) and cytokine/chemokine expression by macrophages (FIG. 1H), whereas all-thiol-HMGB1 does not. However, the influence of redox modifications on the chemotactic activity of HMGB1 was not known. The authors recently showed that HMGB1-induced recruitment of inflammatory cells depends on the formation of a HMGB1-CXCL12 heterocomplex that acts exclusively through CXCR4 and not through other HMGB1 receptors (10). Using a hybrid ELISA (anti-CXCL12 capture antibody and anti-HMGB1 detection antibody) the authors found that all-thiol-HMGB1 forms the heterocomplex with CXCL12; no heterocomplex formation could be detected between disulfide HMGB1 and CXCL12 (FIG. 2A). All-thiol-HMGB1 synergizes with CXCL12 in inducing human monocyte migration, as expected (10), while disulfide-HMGB1 does not (FIG. 2B).

Figure 2C:
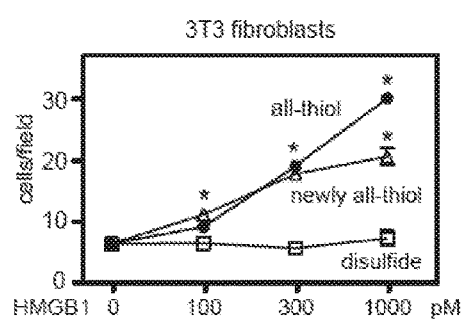
(FIG. 2C) Migration of mouse 3T3 fibroblasts towards disulfide-HMGB1 or all-thiol-HMGB1, or disufide-HMGB1 exposed to 5 mM of DTT for 30 minutes (newly all-thiol-HMGB1) (*, P<0.05 vs. disulfide HMGB1; ANOVA).

Fibroblasts, respond to lower concentrations of HMGB1 compared to leukocytes (11) and support their own migration by secreting CXCL12 both basally and in response to HMGB1 activation of the Receptor for Advanced Glycation Endproducts (RAGE) (10). Mouse 3T3 fibroblasts migrated in a dose-dependent manner towards all-thiol-HMGB1, but not towards disulfide-HMGB1 (FIG. 2C). Notably, the addition of DTT to disulfide-HMGB1 (newly all-thiol HMGB1) restored almost completely the chemotactic activity of the protein.

Taken together, the authors' results indicate that the formation of the C23-C45 disulfide bond inhibits the chemoattractant function of HMGB1 (Table I).

TABLE I.

Summary of HMGB1 redox status vs. activity.
Mutually exclusive redox forms of HMGB1 promote cell recruitment or proinflammatory cytokine release: reduced cysteines make HMGB1 a chemoattractant, a disulfide bond makes it a proinflammatory cytokine and further oxidation of its cysteines to sulfonates by reactive oxygen species abrogates both activities.

| Molecule / Cysteine redox level | Schematic molecular overview | Cytokine-inducing activity | Chemo-attractant activity |
|---|---|---|---|
| all-thiol-HMGB1 CySH | $-C_{23}-C_{45}-C_{106}-$ <br> $\vert$ $\vert$ $\vert$ <br> SH  SH  SH | No | Yes |
| disulfide-HMGB1 CyS-SyC | S——S <br> $\vert$ $\vert$ <br> $-C_{23}-C_{45}-C_{106}-$ <br> $\vert$ <br> SH | Yes | No |
| HMGB1 terminally oxidized by ROS CySo3- | $-C_{23}-C_{45}-C_{106}-$ <br> $\vert$ $\vert$ $\vert$ <br> $SO_3H$ $SO_3H$ $SO_3H$ | No | No |

Figure 2D:
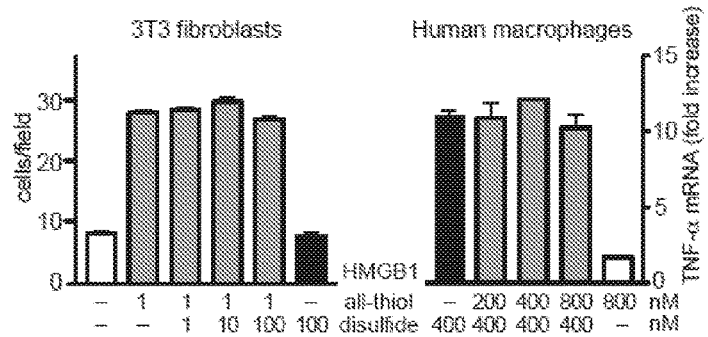
(FIG. 2D) Migration of 3T3 fibroblasts towards all-thiol-HMGB1 in the presence of increasing concentrations of disulfide-HMGB1, and expression of TNF-α (as fold increase compared to unstimulated macrophages) in human macrophages stimulated for 4 hours with disulfide-HMGB1 in the presence of increasing concentrations of all-thiol-HMGB1. The effects of the competing form of HMGB1 are not statistically significant (ANOVA).

Thus, the cytokine-stimulating and chemoattractant activities of HMGB1 are mutually exclusive. In addition, disulfide-HMGB1 and all-thiol-HMGB1 do not compete with each other (FIG. 2D). Indeed, the chemoattractant and cytokine-stimulating functions of HMGB1 require different receptors: CXCR4 and TLR4, respectively (3-5,10). The small conformational rearrangements associated with the formation of a single disulfide bond decrease but not abrogate the binding of HMGB1 to DNA (12), how they can segregate and restrict so effectively the interactions of the all-thiol- and disulfide-HMGB1 to CXCL12 and TLR4, respectively, still needs to be investigated.

Figure 2E:
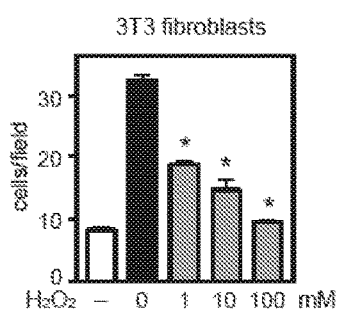
(FIGS. 2E-F) Migration of mouse 3T3 fibroblasts towards wt all-thiol-HMGB1 previously exposed to increasing concentrations of $H_2O_2$ for 1 hour (FIG. 2E) (*, P<0.05 vs. all-thiol HMGB1 not treated with $H_2O_2$, ANOVA), and towards wt all-thiol-HMGB1 or the E106 mutant (SEQ ID No. 1 in which C106 is replaced by glutamine) in which purified in the presence of DTT (FIG. 2F) (*, P<0.05 vs. untreated control).
Figure 2F:
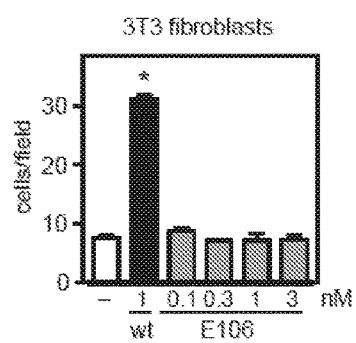
Figure 2G:
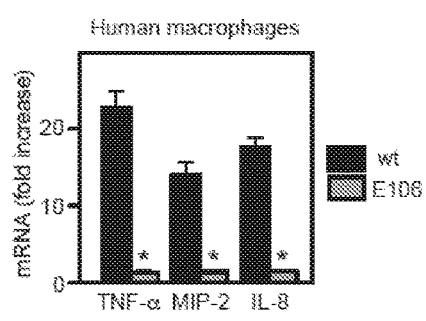
(FIG. 2G) Human macrophages were stimulated for 4 hours with wt disulfide-HMGB1 or the E106 mutant (0.4 μM) prepared in the absence of DTT. Expression of TNF-α, MIP-2 and IL-8 was measured by real-time PCR and expressed as fold increase compared to unstimulated macrophages (*, P<0.05 vs. disulfide-HMGB1; t test). In all panels, data are representative of at least three independent experiments and bars represent the mean±SD of triplicate samples (when not visible, they fall within symbols)

Reactive oxygen species (ROS) abrogate the proinflammatory activity of HMGB1 by terminally oxidizing its cysteines to sulfonates (4,5,13). The authors show that HMGB1 exposed to $H_2O_2$ has no chemotactic activity (FIG. 2E). Thus, terminal oxidation makes HMGB1 inactive, both as proinflammatory and chemotactic factor (Table I). In order to mimic irreversible oxidation to sulfonate, C106 was replaced by a glutamic acid. The electrophoretic mobility of mutant E106 in reducing and non-reducing conditions was identical to that of wt HMGB1 (data not shown). Whereas wt all-thiol-HMGB1 has optimal chemotactic activity on fibroblasts at 1 nM, the E106 mutant, either exposed to DTT or not, was ineffective up to 3 nM (FIG. 2F); it also failed to induce cytokine/chemokine expression by macrophages (FIG. 2G). Moreover, the E106 mutant cannot compete with wt all-thiol- and disulfide-HMGB1 in migration and inflammation assays respectively (data not shown), suggesting that the E106 mutant cannot bind to HMGB1 receptors.

Overall the authors' results demonstrate that the activities of HMGB1 are redox-dependent. After the original description of HMGB1-induced cytokine release by macrophages (Andersson et al., 2000), several studies could not reproduce these results, leading to conclude that HMGB1 can only act in synergy with other inflammatory mediators (14-17). The authors rather conclude that inconsistent results were obtained by using inconsistently defined forms of HMGB1. In order to understand pathogenesis, it will be important to consider which HMGB1 is present in each specific condition and locale in vivo.

Figure 3A:
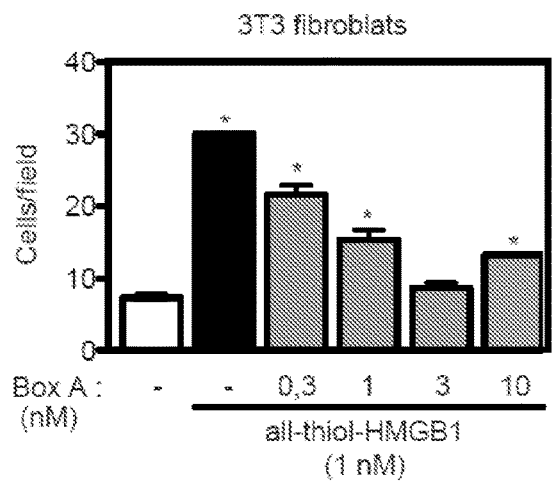
(FIG. 3A, FIG. 3C) Migration of mouse 3T3 fibroblasts towards wt all-thiol-HMGB1 in the presence or not of BoxA (FIG. 3A) or F(ab')₂ fragments from the DPH1.1 anti-HMGB1 monoclonal antibody (FIG. 3C).
Figure 3B:
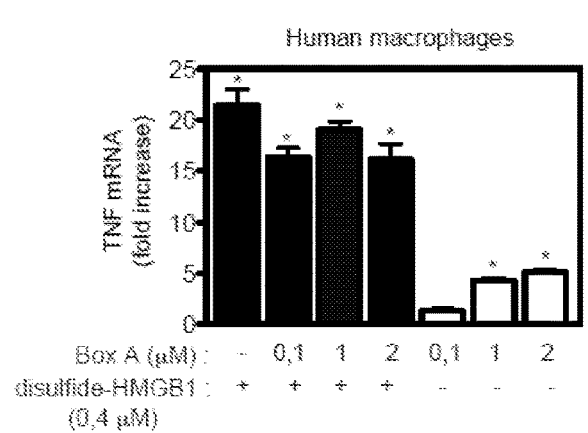
(FIG. 3B, FIG. 3D) Human macrophages were stimulated for 4 hours with disulfide-HMGB1 (0.4 μM) in the presence of BoxA (FIG. 3B) or DPH1.1 F(ab')₂ fragments (FIG. 3D). Expression of TNF-α was measured by real-time PCR and expressed as fold increase compared to unstimulated macrophages. In all panels, data are representative of at least three independent experiments and bars represent the mean±SD of triplicate samples (*, P<0.05 vs. control; ANOVA)
Figure 3C:
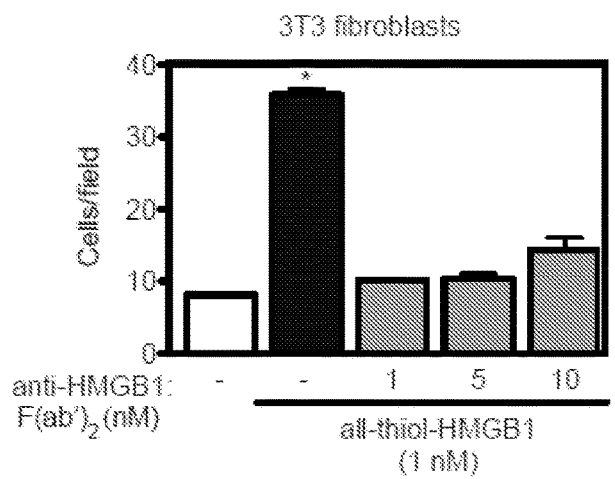
Figure 3D:
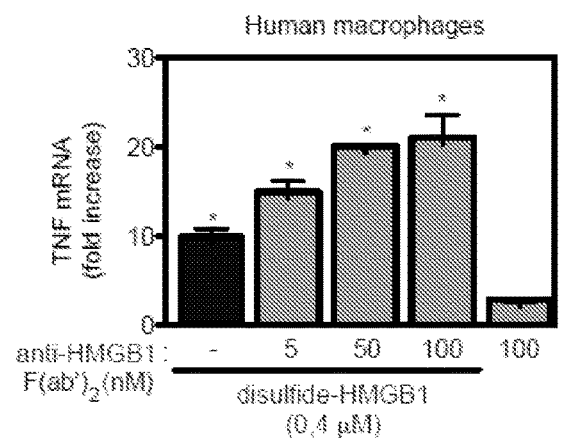

HMGB1 Inhibitors BoxA and Monoclonal Antibody DPH1.1 Prevent Cell Migration but not Cytokine Production Several inhibitors of HMGB1 have been developed, among which the most commonly used are monoclonal antibodies and BoxA; the authors investigated whether they block HMGB1's chemoattractant and/or cytokine-inducing activities. BoxA inhibited in a dose-dependent manner the migration of fibroblasts in response to HMGB1 but failed to prevent HMGB1-induced TNF-α expression in macrophages (FIGS. 3A-3B). The authors also tested the activity of the monoclonal antibody DPH1.1, directed against an epitope between BoxB and the acidic tail of HMGB1 (18). The authors prepared F(ab')$_2$ fragments to avoid the unspecific activation of macrophages: they inhibit HMGB1-induced cell migration but not TNF-α expression (FIGS. 3C-3D). Previous studies have demonstrated that a different anti-HMGB1 monoclonal antibody (2G7) inhibits HMGB1-induced cytokine formation in macrophages (Yang et al., 2010). Thus, it is possible to neutralize the chemoattractant activity of HMGB1 without interfering with the cytokine-inducing activity. In fact, the known therapeutic effects of BoxA in models of hepatitis (19), peritonitis (20), ischemia/reperfusion of the heart and the brain (21,22), and others, may be entirely attributable to the reduced recruitment of inflammatory cells in the injured tissue.

Figure 4A:
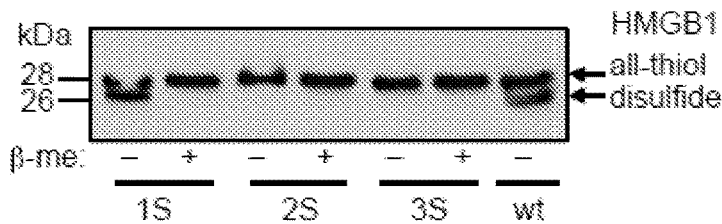
(FIG. 4A) Electrophoretic mobility of recombinant wt HMGB1 and mutants prepared in the absence of DTT, determined as described in the legend of FIG. 1F.
Figure 4B:
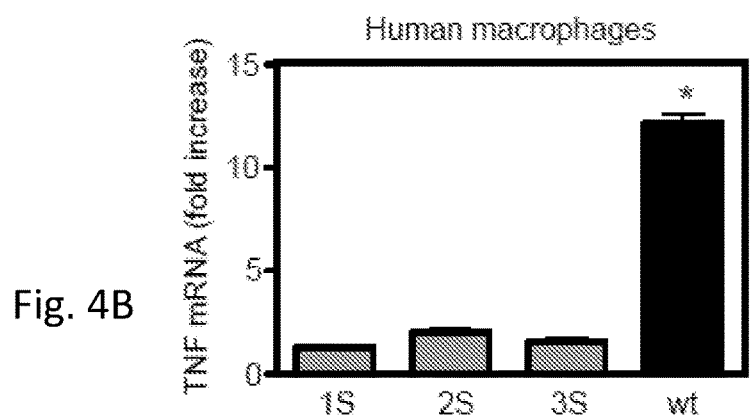
(FIG. 4B) Human macrophages were stimulated for 4 hours with mutants or wt HMGB1 prepared in the absence of DTT (0.4 μM). TNF-α expression was measured by real-time PCR (*, P<0.05 vs. control, ANOVA).
Figure 4C:
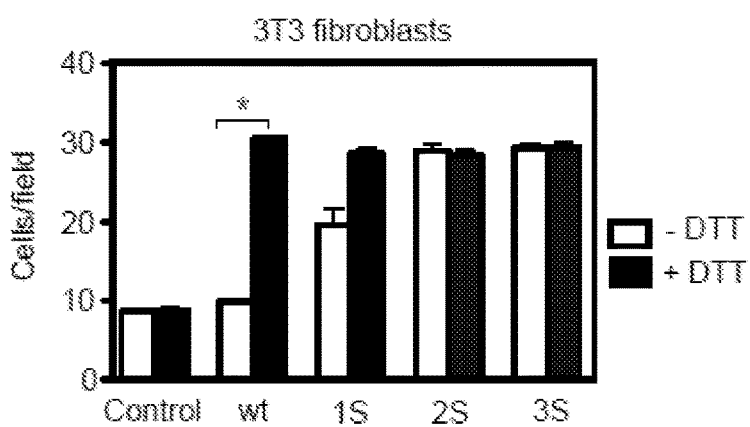
(FIG. 4C-4D) 3T3 fibroblast migration toward 1 nM HMGB1 mutants, exposed or not for 1 hour to 5 mM DTT (C) or to 100 mM $H_2O_2$ (D). Bars represent the mean±SD of triplicate samples (*, P<0.05 vs. control, ANOVA).
Figure 9A:
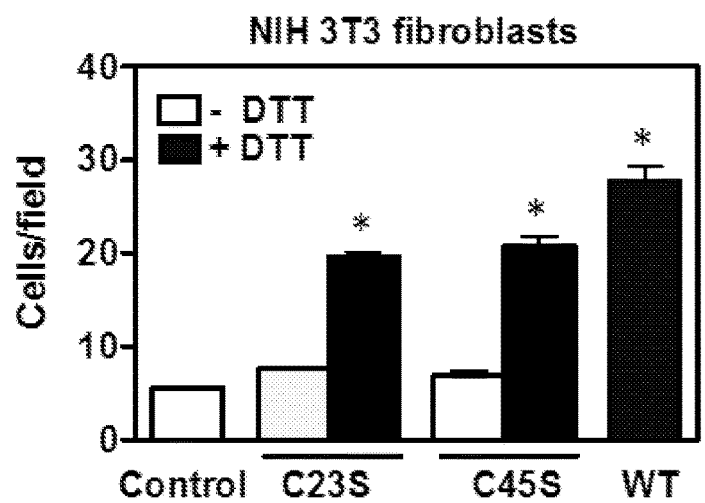
(FIG. 9A) 3T3 fibroblast migration toward 1 nM HMGB1 wt or mutants (C23S, C45S) exposed or not for 1 hour to 5 mM DTT. Bars represent the mean±SD of triplicate samples (*, P<0.05 vs. control, ANOVA).
Figure 9B:
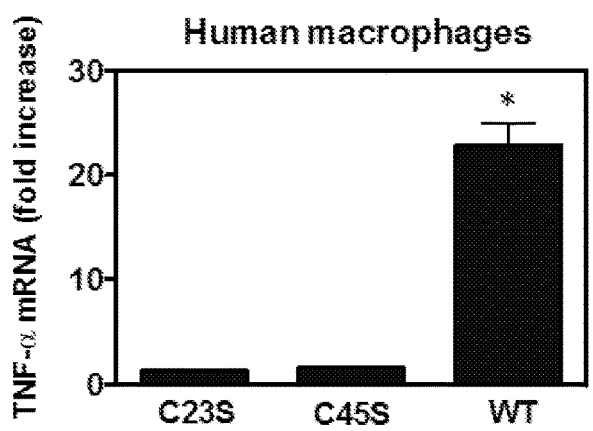
(FIGS. 9B-9C) Human macrophages were stimulated for 4 hours with wt HMGB1 or mutants C23S and C45S (FIG. 9B) or C23-45S and C45-106S (FIG. 9C) prepared in the absence of DTT (0.4 µM). TNF-α expression was measured by real-time PCR (*, P<0.05 vs. control, ANOVA).
Figure 9C:
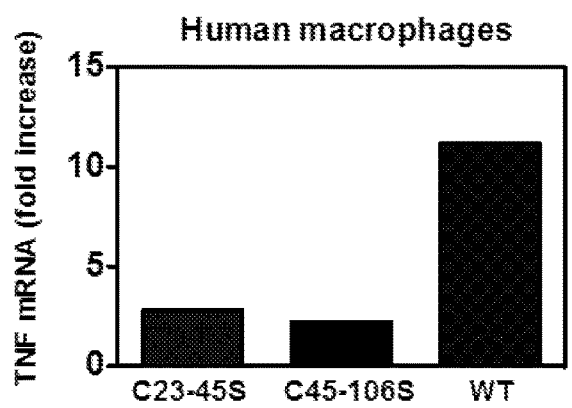

The Three HMGB1 Cysteine Residues are Required for the Cytokine-Stimulating Activity but not for the Chemoattractant Activity In order to study the involvement of individual cysteines in the activities of HMGB1, the authors generated mutants 1S-HMGB1 (where C106 is replaced by a serine), 2S-HMGB1 (where C23 and C45 are replaced), and 3S-HMGB1 (where all 3 cysteines are replaced). All mutants were purified without DTT, and were reduced where indicated by exposure to 5 mM DTT. Electrophoretic mobility showed the presence of the C23-C45 disulfide bond in 1S-HMGB1, but not in 2S-HMGB1 and 3S-HMGB1 (FIG. 4A). All mutants failed to induce TNF-α expression in macrophages, but they all induced fibroblast migration (FIGS. 4B-4C). Similar results were observed with mutants C23S, C45S or C45-106S (FIG. 9). As expected 2S- and 3S-HMGB1 had the same chemotactic activity whether exposed to DTT or not, since there is no disulfide bond that can be reduced. Thus, each cysteine is required for the cytokine-stimulating activity but none for the chemoattractant activity of HMGB1.

Figure 4D:
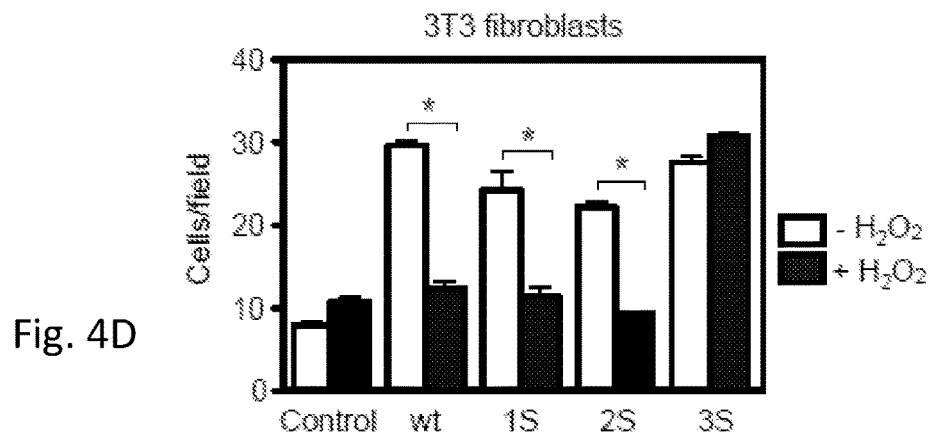

The authors next investigated if the chemotactic activity of the mutants was abrogated by ROS. As expected, treatment with $H_2O_2$ abrogated the chemotactic activity of 1S- and 2S-HMGB1, but not of 3S-HMGB1, which has no cysteine that can be terminally oxidized (FIG. 4D).

Cysteine Oxidation Modulates the Different Functions of HMGB1 In Vivo

Many studies have shown that during inflammation ROS production supports an extracellular oxidative environment, causing the formation of disulfide bonds between thiols (23,24). High ROS levels produced during apoptosis cause terminal oxidation of HMGB1, redirecting its ability to activate acquired immune response towards tolerance (13). A previous study suggested that HMGB1 released by necrotic cells also gets oxidized (25). Finally, HMGB1 has been shown to be a redox sensor in the context of autophagy (26). Thus, the authors investigated whether the redox state of HMGB1 depends on its source.

HMGB1 is released passively into the extracellular medium during necrosis and is secreted actively by monocytes and macrophages after stimulation with LPS and ATP (Gardella et al., 2002). The authors characterized by LC-MS/MS the redox state of HMGB1 before and after release by THP-1 cells (Table II).

TABLE II

Redox status of intracellular and extracellular HMGB1 in THP-1 cells. Mass spectrometric characterization of the redox state of HMGB1 cysteines in the nucleus, the cytosol and the supernatant of THP-1 cells. HMGB1 from cells treated or not with LPS and from the supernatant of was analysed by LC-MS/MS.

| Intracellular HMGB1 | | | | Extracellular HMGB1 | |
|---|---|---|---|---|---|
| Control | LPS | Control | LPS | LPS | Necrotic medium |
| Nucleus | | Cytosol | | Supernatant | |
| all-thiol HMGB1 | | | | all-thiol HMGB1 + disulfide-HMGB1 | |

The HMGB1 contained inside the cell (nucleus or cytosol) is completely reduced, also when THP-1 cells are exposed to LPS. Notably, the supernatants from THP-1 cells mechanically necrotized with freeze-thaw cycles or from cells secreting HMGB1 after LPS exposure contained both all-thiol- and disulfide-HMGB1. Thus, the authors identified monocytic cells as a source of disulfide-HMGB1; activated monocytes may participate to the inflammatory response by producing the cytokine-stimulating HMGB1.

Figure 5A:
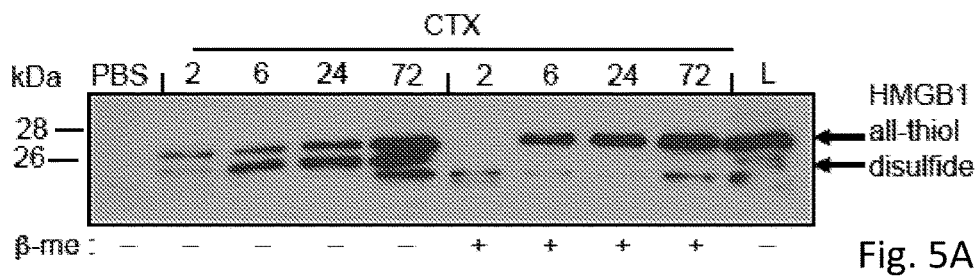
(FIG. 5A) Electrophoretic mobility of HMGB1 from tibialis anterior muscles harvested at the indicated times (2, 6, 24 and 72 h) after cardiotoxin (CTX) injection. Samples were heated in the presence (+) or absence (−) of 350 mM β-mercaptoethanol (β-me), loaded onto a 12% SDS-PA gel and revealed by Western blotting using a polyclonal antibody against HMGB1. Total lysate of tibialis anterior muscle was added as a control (L).

The authors then investigated the redox state of HMGB1 in vivo during muscle injury and the subsequent sterile inflammation, using electrophoretic mobility as an assay. Tibialis anterior muscles of mice were damaged or not by cardiotoxin (CTX) injection, which causes muscle cell necrosis (27). Muscles were harvested 2, 6, 24 or 72 hours after CTX injection and incubated in PBS with Collagenase D (FIG. 5A). HMGB1 was barely detectable in the medium bathing healthy muscles but was abundant in the medium bathing CTX-injured muscles. At early time points (2 h) all-thiol-HMGB1 was detected, but from 6 hours disulfide-HMGB1 appeared. It is possible that infiltrating inflammatory cells secrete disulfide-containing HMGB1, as the authors observed in vitro with monocytic cells (Table II). Indeed, leukocytes are recruited into damaged muscle already 3 hours after CTX injection (10). A non-mutually exclusive explanation is that the infiltrating cells, a well-known source of ROS, may induce the oxidation of HMGB1 released by the damaged tissue. Moreover, disulfide-HMGB1 is not present in the healthy muscle as demonstrated by the lysate control. Thus, disulfide-HMGB1 can be considered as a marker of tissue damage.

Figure 5B:
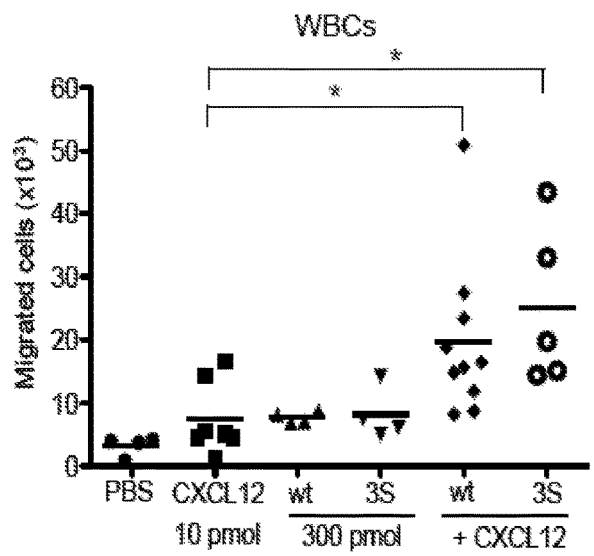
(FIG. 5B-5D) 3S-HMGB1 induces leukocyte recruitment in vivo. An air-pouch was created in mice by the dorsal subcutaneous injection of air. At day 6, the air pouches were injected with 200 μl of PBS containing 10 pmol CXCL12, 300 pmol HMGB1 (wt or 3S) or both.
Figure 5C:
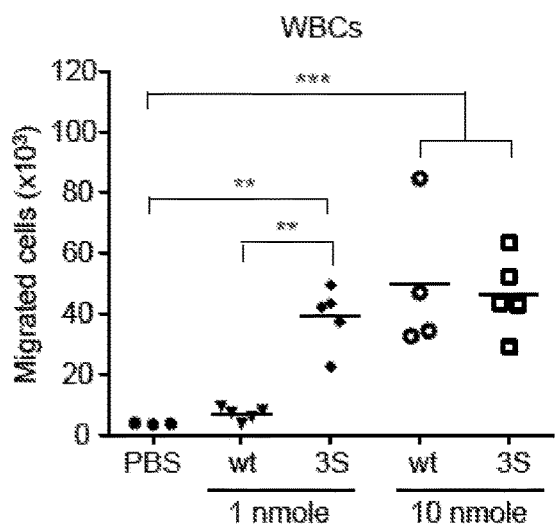
Figure 5D:
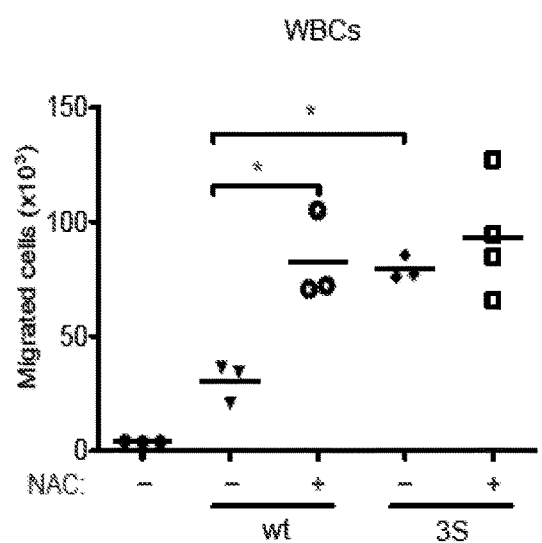
Figures 6A, 6B:
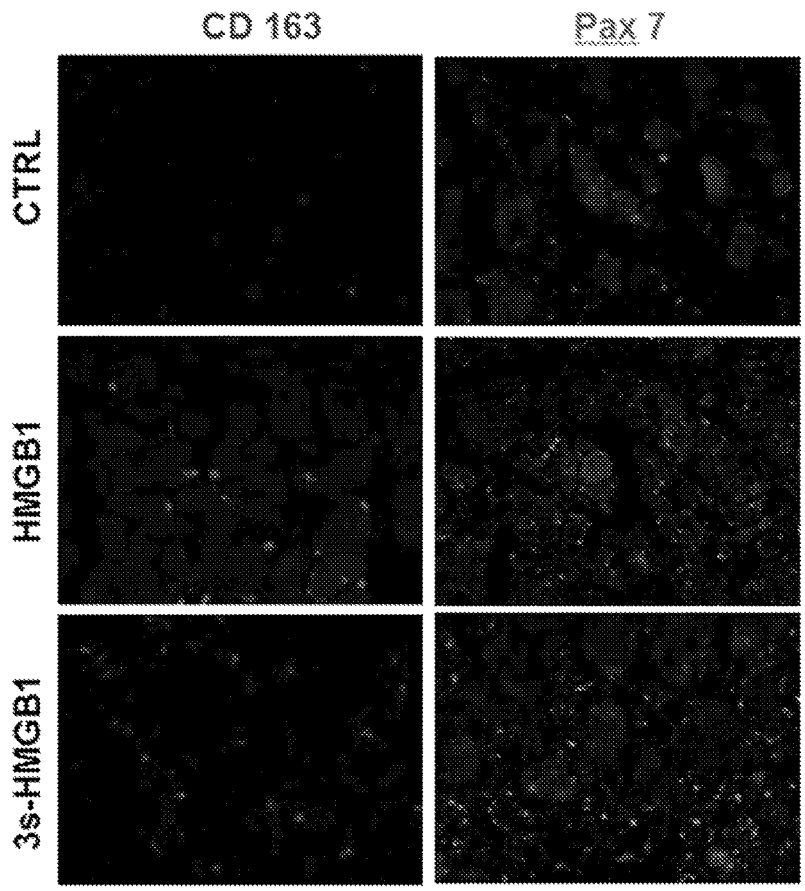
(FIGS. 6A-6B) Immunofluorescence staining of macrophages M2c (CD163, red) on sections of TA muscles 2 days after the intramuscular injection of cardiotoxin and HMGB1 (wt or 3S).
Figure 6C:
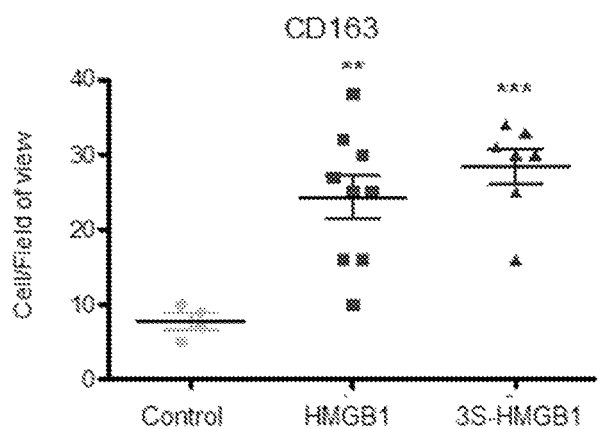
(FIGS. 6C-6D) Quantification of macrophages M2 (upper panel) and satellite cells (lower panel) performed on 20 random sections per sample. =p<0.01; *p<0.001.
Figure 6D:
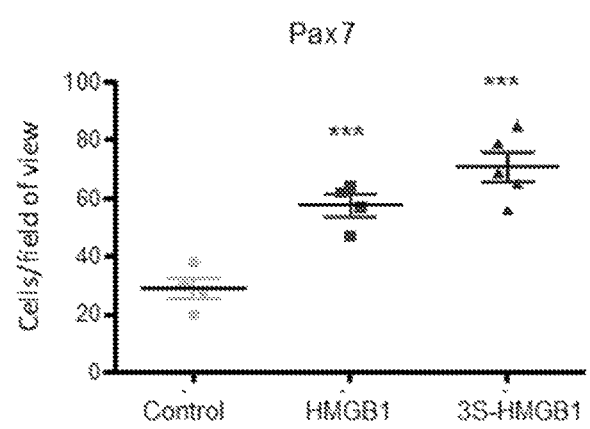

Since 3S-HMGB1 is resistant to oxidation, the authors hypothesized that its activity in vivo should not be modified by ROS production. The authors previously showed (10)

that the HMGB1/CXCL12 heterocomplex induces a massive influx of leukocytes into air pouches created by the injection of air in the dorsal derma of mice; such air pouches provide a cavity into which drugs can be administered and from which recruited cells can be recovered. The authors injected into air-pouches wt or 3S-HMGB1 (300 pmol) together with CXCL12 (10 pmol). HMGB1 (wt or 3S) or CXCL12 alone failed to induce leukocyte recruitment, but both wt and 3S-HMGB1 in association with CXCL12 induced a massive influx of leukocytes (FIG. 5B). Notably, the number of recruited leukocytes was increased in response to 3S-HMGB1/CXCL12 compared to wt HMGB1/CXCL12. Since a low amount of CXCL12 is always present in the extracellular fluids, and HMGB1 can induce the secretion of additional CXCL12 (10), the authors also performed the air-pouch experiments using high concentrations of HMGB1 alone. The injection into the air pouch of 1 nmol 3S-HMGB1 induced leukocyte recruitment, but the equivalent amount of all-thiol wt HMGB1 had no effect (FIG. 5C). However, still higher doses of all-thiol wt or 3S-HMGB1 (10 nmol) both recruited leukocytes, with no significant difference. This is compatible with stoichiometric inactivation of HMGB1 by ROS produced in situ. To confirm this hypothesis the authors performed the same experiment in the presence or not of N-acetylcysteine (NAC), an antioxidant (FIG. 5D). The authors observed that 1 nmol wt protein induced leukocyte recruitment as effectively as 3S-HMGB1 in the presence of NAC, demonstrating that wt HMGB1 gets inactivated in vivo by ROS-induced oxidation.

Taken together, in vitro and in vivo experiments show that 3S-HMGB1 can induce leukocyte recruitment without inducing cytokine/chemokine production and is also resistant to terminal oxidation by ROS. HMGB1 has been shown to promote regeneration in several models of tissue damage, and all such experiments were performed with the reduced form of recombinant wt HMGB1 (28). However, the redox states of HMGB1 administered in vivo may interconvert among each other.

3S-HMGB1 Limits Muscle Damage and Favours Muscle Regeneration after Injury

HMGB1 is also likely to be involved in tissue regeneration after inflammation resolution. It was shown that blockage of HMGB1 retards the healing of skin wounds. In some conditions where wound closure is compromised, for example in diabetic mice, administration of additional HMGB1 can promote wound closure (29). Moreover, administration of HMGB1 after myocardial infarction promotes the healing of the infarcted area and functional recovery of the heart (30). Finally, HMGB1 is pro-angiogenic and promotes revascularization of muscle after ischemia (31). Since the tissue microenvironment turns reducing during tissue regeneration (32), it can be expected that the form of HMGB1 that favors regeneration is the one containing reduced cysteines. The tissue microenvironment, in particular in muscle (34), becomes reducing in order to favor tissue regeneration. Thus, the authors propose that the all-thiol form of HMGB1 is the one required for tissue regeneration.

Figure 7:
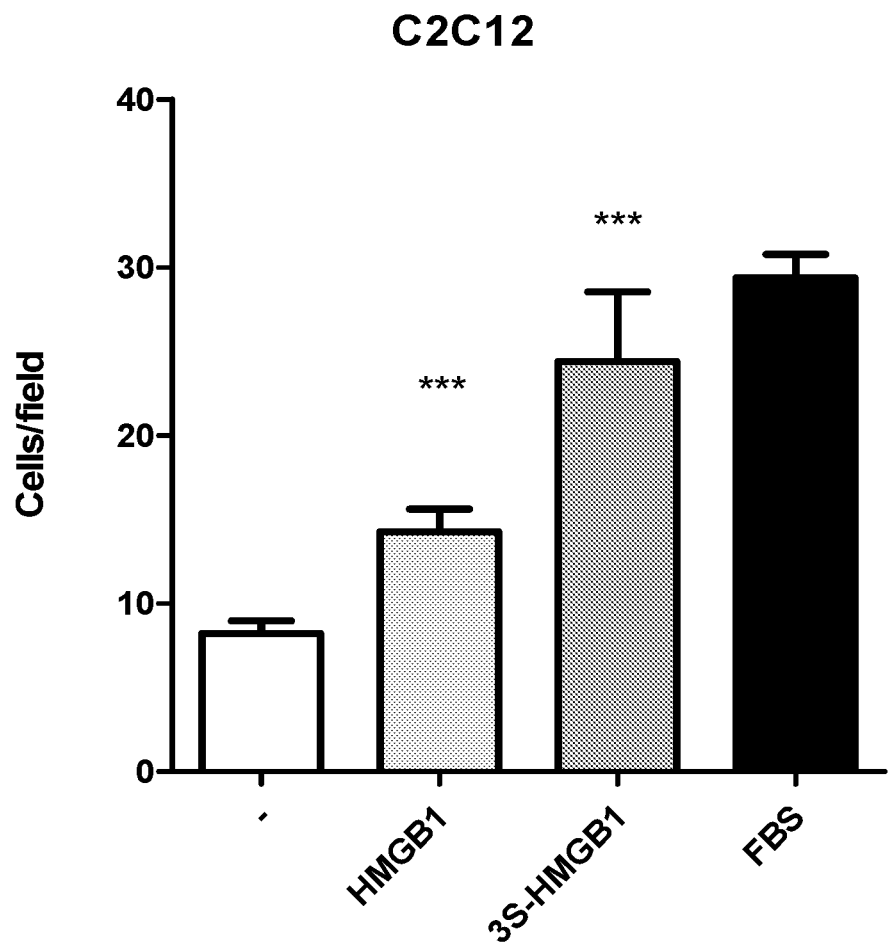
FIG. 7. HMGB1 induces the migration of myoblasts in vitro. Migration of myogenic C2C12 cells towards wt or 3S-HMGB1 (1 µM) in modified boyden chambers (***, P<0.001 vs. control; ANOVA). Foetal Bovine Serum (FBS) as positive control.

3S-HMGB1 might mimic all-thiol HMGB1 and favour tissue regeneration. To prove this, the authors have tested 3S-HMGB1 in a mouse model of muscle regeneration after acute injury. Interestingly, injection of all-thiol HMGB1 or 3S-HMGB1 in tibialis anterior (TA) muscles together with cardiotoxin significantly increases the number of M2 macrophages (identified by the presence of the CD163 surface marker), which are proangiogenic and tissue-regenerating. The number of satellite cells (evidenced by the expression of the Pax-7 transcription factor), that are the resident progenitor cells which can regenerate muscle fibers is also significantly increased (FIG. 7). Notably, injection of 3S-HMGB1 is more effective than natural unmodified HMGB1.

Figure 8:
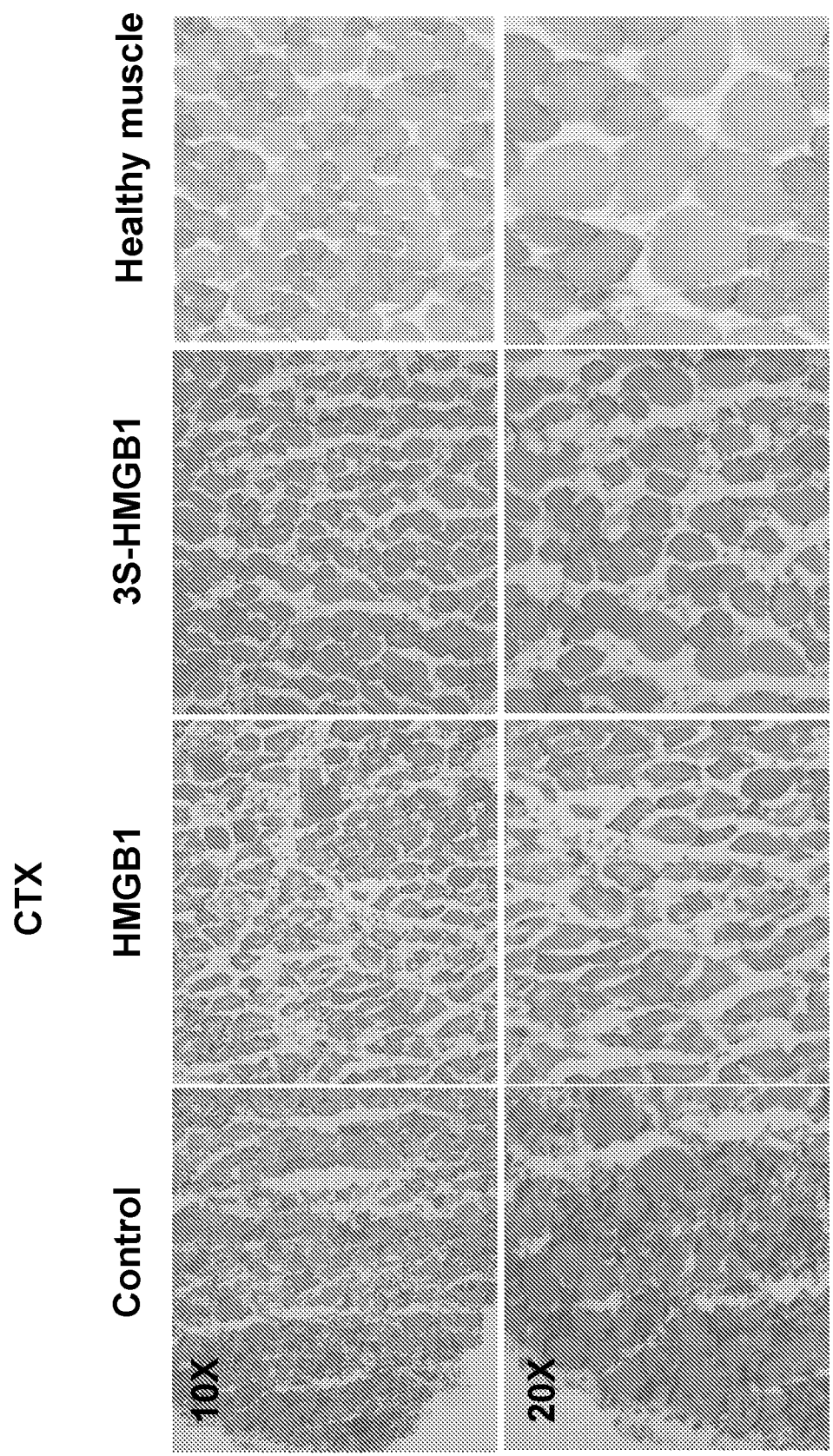
FIG. 8. Preservation of the muscle structure by HMGB1 after acute muscle injury. Muscle injury was performed on the tibialis anterior (TA) of 8-weeks-old C57BL/6 by injecting 50 µl of 10 µM CTX in presence or not of 150 µg HMGB1 (wt or 3S) (three animals per group). Representative sections of TA muscles from treated and untreated mice stained with Hematoxylin & Eosin 2 days after CTX injury.

Motility of myogenic cells is required for the regeneration of damaged muscle. One explanation for the increased number of satellite cells observed in mice injected with HMGB1 could be their recruitment from nearby muscles. Indeed, 3S-HMGB1 and to a lesser extent natural unmodified all-thiol HMGB1 are strong chemoattractants for C2C12 cells, which are a cell line similar to myoblasts (FIG. 8).

Thus, 3S-HMGB1 displays favourable properties for the regeneration of damaged muscle. Similarly 1S-HMGB1 and 2S-HMGB1 have therapeutic properties for the regeneration of damaged muscle, however to a lesser extend compared to 3 S-HMGB1.

Surprisingly, however, an additional favourable property of 3S-HMGB1 was noticed upon examination of TA muscles 2 days after CTX-induced injury. Muscles injected with both natural unmodified all-thiol HMGB1 or 3S-HMGB1 appeared less severely damaged than control muscles, as evidenced by H&E staining (FIG. 9). Inflammatory infiltrating cells were fewer, and, in particular in mice injected with 3S-HMGB1, muscle fibers appeared more numerous and larger than in control CTX-injected muscle. Several of these fibers contained peripherally located nuclei, indicative that the fibers were mature, rather than regenerating. Thus, 3S-HMGB1 limit muscle damage and fiber death immediately after the injury, in addition to favouring its regeneration at longer times.

Use of 3S-HMGB1 in Limiting Myocardial Damage and Favouring Healing after Infarction HMGB1 has already been shown to improve the functional recovery of the heart after infarction (30). In this case, the histological appearance of the area subject to hypoxia reperfusion and injected with all-thiol HMGB1 appears much improved, with the notable presence of cardiomyocytes in vastly larger numbers compared to non-HMGB1-injected controls. In light of the results reported in the previous section with skeletal muscle, cardiac muscle cells might be prevented from dying immediately after the damage. 3S-HMGB1 may be used with superior effects compared to wt HMGB1 to limit damage and favour healing after myocardial infarction. 1S-HMGB1 and 2S-HMGB1 may be also be used.

Use of 3S-HMGB1 in Limiting Hard Tissue Damage and Favouring Healing after Injury HMGB1 has been involved in the development of bone and cartilage (33). Since the ontology of muscle, bone and cartilage cells is common, indeed all of these cells are of mesodermal origin deriving from somites and since developmental processes are routinely used in adult life for the repair and regeneration of damaged tissue, 3S-HMGB1 may be useful in limiting damage and favouring healing after injury of bones and cartilages, including those deriving from fractures.

In conclusion, the authors show that the Damage Associated Molecular Pattern (DAMP) activities of HMGB1—recruitment of leukocytes and their activation to secrete pro-inflammatory cytokines—depend on different and mutually exclusive redox states of the same polypeptide, which can be modified within the injured tissue after its release. The authors show that non-oxidizable forms of HMGB1 can recruit cells, both parenchymal and from the circulation, but do not elicit inflammation. Injection of a non-oxidizable form of HMGB1 in skeletal muscle after damage does not polarize inflammatory cells toward the inflammatory state, but rather towards the M2 reparative state, and surprisingly limits muscle cell death; either or both effects lead to superior muscle regeneration. Given the involvement of HMGB1 in the repair and/or development of heart, bone and cartilage, administration of non-oxidizable forms of HMGB1, in particular 3S-HMGB1 should also lead to improved heart, bone and cartilage tissue repair and healing after damage.

REFERENCES

1. Bianchi, M. E. (2007) *Journal of leukocyte biology* 81, 1-5
2. Andersson, U., and Tracey, K. J. (2012) *Annu Rev Immunol* 30, 313-335
3. Yang, H., et al., (2010) *PNAS* 107, 11942-11947
4. Yang, H., et al., (2011) *Molecular medicine*
5. Yang, H., et al., (2012) *Mol Med* 18, 250-259
6. Knapp, S., et al., (2004) *Biochemistry* 43, 11992-11997
7. Antoine, D. J., et al., (2009) *Toxicol Sci* 112, 521-531
8. De Lorenzi, R., et al., (2009) *Genesis* 47, 323-329
9. Sung, M. H., et al., (2009) *PLoS One* 4, e7163
10. Schiraldi, M., et al., (2012) *J Exp Med* 209, 551-563
11. Palumbo, R., et al., (2007) *The Journal of cell biology* 179, 33-40
12. Park, S., and Lippard, S. J. (2011) *Biochemistry* 50, 2567-2574
13. Kazama, H., et al., (2008) *Immunity* 29, 21-32
14. Andersson, U., et al., (2000) *J Exp Med* 192, 565-570
15. Li, J., et al., (2004) *J Immunol Methods* 289, 211-223
16. Bianchi, M. E. (2009) *J Leukoc Biol* 86, 573-576
17. Youn, J. H., et al., (2008) *J Immunol* 180, 5067-5074
18. Sitia, G., et al., (2011) *PLoS pathogens* 7, e1002061
19. Sitia, G., et al., (2007) *J Leukoc Biol* 81, 100-107
20. Orlova, V. V., et al., (2007) *The EMBO journal* 26, 1129-1139
21. Andrassy, M., et al., (2008) *Circulation* 117, 3216-3226
22. Muhammad, S., et al., (2008) *J Neurosci* 28, 12023-12031
23. Rubartelli, A., and Sitia, R. (2009) *Antioxidants & redox signaling* 11, 2621-2629
24. Carta, S., et al., (2009) *Journal of leukocyte biology* 86, 549-555
25. Urbonaviciute, V., et al., (2009) *Autoimmunity* 42, 305-307
26. Kang, R., et al., (2011) *Autophagy* 7, 904-906
27. Ownby, C. L., Fletcher, J. E., and Colberg, T. R. (1993) *Toxicon* 31, 697-709
28. Biscetti, F., et al., (2011) *Current vascular pharmacology* 9, 677-681
29. Straino, S., et al., (2008) *J Invest Dermatol* 128, 1545-1553
30. Limana, F., et al., (2005) *Circ Res* 97, e73-83
31. De Mori, R., et al., (2007) *Arterioscler Thromb Vasc Biol* 27, 2377-2383
32. Vezzoli, M., et al., (2010) *Ann N Y Acad Sci* 1209, 83-90
33. Taniguchi, N., et al., (2007) *Mol Cell Biol* 27, 5650-5663
34. Vezzoli M. et al, (2011) *Antioxid Redox Signal* 15(8), 2161-74

The invention claimed is:

1. A method for treating injured skeletal muscle or fractured bone in a subject in need thereof, the method comprising administering to the subject an amount of a High Mobility Group Box 1 (HMGB1) variant effective to promote healing of injured skeletal muscle or fractured bone, wherein the variant HMGB1 consists of SEQ ID NO: 1, wherein cysteine residues at positions 23, 45, and 106 of SEQ ID NO: 1 are replaced by serine residues.

2. The method of claim 1, wherein the HMGB1 variant is a cell chemoattractant that does not stimulate cytokine and/or chemokine production from a cell.

3. The method of claim 1, wherein the HMGB1 variant will not induce TNF expression in macrophages.

4. The method of claim 1, wherein the HMGB1 variant is administered to the subject systemically.

5. The method of claim 1, wherein the HMGB1 variant is administered to the subject by local injection to the muscle or bone to be treated.

6. A method for limiting damage to muscle in a subject having muscle that has been injured, comprising administering to the subject an effective amount of a High Mobility Group Box 1 (HMGB1) variant, wherein the variant HMGB1 consists of SEQ ID NO: 1, wherein cysteine residues at positions 23, 45, and 106 of SEQ ID NO: 1 are replaced by serine residues.

7. The method of claim 6, wherein the HMGB1 variant is administered to the subject by local injection to the muscle.

8. The method of claim 6, wherein the HMGB1 variant is administered to the subject systemically.

9. The method of claim 6, wherein the muscle is skeletal muscle.

* * * * *

SEQUENCE LISTING

```
<160> NUMBER OF SEQ ID NOS: 13

<210> SEQ ID NO 1
<211> LENGTH: 215
<212> TYPE: PRT
<213> ORGANISM: Homo sapiens

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160
```

Ala Tyr Arg Ala Lys Gly Lys Pro Asp Ala Lys Lys Gly Val Val
            165                 170                 175

Lys Ala Glu Lys Ser Lys Lys Lys Glu Glu Glu Asp Glu Glu
        180                 185                 190

Asp Glu Glu Asp Glu Glu Glu Glu Asp Glu Glu Asp Glu Asp Glu
            195                 200                 205

Glu Glu Asp Asp Asp Asp Asp
    210                 215

<210> SEQ ID NO 2
<211> LENGTH: 215
<212> TYPE: PRT
<213> ORGANISM: Rattus norvegicus

<400> SEQUENCE: 2

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
            165                 170                 175

Lys Ala Glu Lys Ser Lys Lys Lys Glu Glu Glu Asp Asp Glu Glu
        180                 185                 190

Asp Glu Glu Asp Glu Glu Glu Glu Asp Glu Glu Asp Glu Asp Glu
            195                 200                 205

Glu Glu Asp Asp Asp Asp Glu
    210                 215

<210> SEQ ID NO 3
<211> LENGTH: 89
<212> TYPE: PRT
<213> ORGANISM: Homo sapiens

<400> SEQUENCE: 3

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

```
Trp Lys Thr Met Ser Ala Lys Glu Lys Gly Lys Phe Glu Asp Met Ala
 50                  55                  60
Lys Ala Asp Lys Ala Arg Tyr Glu Arg Glu Met Lys Thr Tyr Ile Pro
 65                  70                  75                  80
Pro Lys Gly Glu Thr Lys Lys Lys Phe
                 85
```

```
<210> SEQ ID NO 4
<211> LENGTH: 25
<212> TYPE: DNA
<213> ORGANISM: Artificial Sequence
<220> FEATURE:
<223> OTHER INFORMATION: synthetic primer

<400> SEQUENCE: 4
tgacggggtc acccacactg tgccc                                    25

<210> SEQ ID NO 5
<211> LENGTH: 25
<212> TYPE: DNA
<213> ORGANISM: Artificial Sequence
<220> FEATURE:
<223> OTHER INFORMATION: synthetic primer

<400> SEQUENCE: 5
ctagaagcat tgcggtggac gatgg                                    25

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
agcccatgtt gtagcaaacc                                          20

<210> SEQ ID NO 7
<211> LENGTH: 21
<212> TYPE: DNA
<213> ORGANISM: Artificial Sequence
<220> FEATURE:
<223> OTHER INFORMATION: synthetic primer

<400> SEQUENCE: 7
aggacctggg agtagatgag g                                        21

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8 taccccagg agaagattcc                                           20

<210> SEQ ID NO 9
<211> LENGTH: 20
<212> TYPE: DNA
<213> ORGANISM: Artificial Sequence
<220> FEATURE:
<223> OTHER INFORMATION: synthetic primer
```

```
<400> SEQUENCE: 9
ttttcaccag gcaagtctcc                                                  20

<210> SEQ ID NO 10
<211> LENGTH: 18
<212> TYPE: DNA
<213> ORGANISM: Artificial Sequence
<220> FEATURE:
<223> OTHER INFORMATION: synthetic primer

<400> SEQUENCE: 10
tgccaaggag tgctaaag                                                    18

<210> SEQ ID NO 11
<211> LENGTH: 18
<212> TYPE: DNA
<213> ORGANISM: Artificial Sequence
<220> FEATURE:
<223> OTHER INFORMATION: synthetic primer

<400> SEQUENCE: 11
ctccacaacc ctctgcac                                                    18

<210> SEQ ID NO 12
<211> LENGTH: 17
<212> TYPE: DNA
<213> ORGANISM: Artificial Sequence
<220> FEATURE:
<223> OTHER INFORMATION: synthetic primer

<400> SEQUENCE: 12
tgccagtgct tgcagac                                                     17

<210> SEQ ID NO 13
<211> LENGTH: 19
<212> TYPE: DNA
<213> ORGANISM: Artificial Sequence
<220> FEATURE:
<223> OTHER INFORMATION: synthetic primer

<400> SEQUENCE: 13
tcttaaccat gggcgatgc                                                   19
```